(12) United States Patent
Cristau et al.

(10) Patent No.: US 10,244,756 B2
(45) Date of Patent: *Apr. 2, 2019

(54) FUNGICIDAL N-CYCLOALKYL-N-{[ORTHO-(1-SUBSTITUTED-CYCLOALKYL)HETEROARYL]METHYL}(THIO)CARBOXAMIDES

(71) Applicant: Bayer CropScience Aktiengesellschaft, Monheim am Rhein (DE)

(72) Inventors: Pierre Cristau, Lyons (FR); Philippe Desbordes, Lyons (FR); Julie Geist, Lyons (FR); Lionel Nicolas, Lyons (FR); Philippe Rinolfi, Châtillon d'Azergues (FR); Jan Peter Schmidt, Folsom, CA (US); Tomoki Tsuchiya, Lyons (FR)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/575,292

(22) PCT Filed: May 19, 2016

(86) PCT No.: PCT/EP2016/061203
§ 371 (c)(1),
(2) Date: Nov. 17, 2017

(87) PCT Pub. No.: WO2016/184942
PCT Pub. Date: Nov. 24, 2016

(65) Prior Publication Data
US 2018/0146670 A1    May 31, 2018

(30) Foreign Application Priority Data

May 21, 2015 (EP) .................................... 15290134

(51) Int. Cl.
| *A01N 43/56* | (2006.01) |
| *C07D 401/12* | (2006.01) |
| *C07D 409/12* | (2006.01) |

(52) U.S. Cl.
CPC ........... *A01N 43/56* (2013.01); *C07D 401/12* (2013.01); *C07D 409/12* (2013.01)

(58) Field of Classification Search
None
See application file for complete search history.

(56) References Cited

FOREIGN PATENT DOCUMENTS

| WO | WO-2008/015189 | 2/2008 |
| WO | WO-2008/037789 | 4/2008 |
| WO | WO-2009/016221 | 2/2009 |
| WO | WO-2009/016222 | 2/2009 |
| WO | WO-2010/130767 | 11/2010 |
| WO | WO-2012/052490 | 4/2012 |
| WO | WO-2012/065944 | 5/2012 |
| WO | WO-2015/082587 | 6/2015 |

OTHER PUBLICATIONS

International Search Report and Written Opinion dated Jun. 22, 2016 for International Application No. PCT/EP2016/061203, filed May 19, 2016, 13 pages.

*Primary Examiner* — Zinna Northington Davis
(74) *Attorney, Agent, or Firm* — Morrison & Foerster LLP

(57) ABSTRACT

The invention relates to fungicidal N-cycloalkyl-N-{[ortho-(1-substituted-cycloalkyl)heteroaryl]methyl}carboxamides and their thiocarbonyl analogs of formula (I), their process of preparation, their use as fungicides, particularly in the form of fungicidal compositions, and methods for the control of phytopathogenic fungi of plants using these compounds or their compositions. A represents a carbo-linked, unsaturated or partially saturated, optionally substituted 5-membered heterocyclyl group; T represents O or S; $Z^1$ represents an optionally substituted $C_3$-$C_7$-cycloalkyl; p represents 1-5; $B^1$ represents a carbo-linked, unsaturated, monocyclic or fused bicyclic 5-, 6-, 8-, 9-, 10-membered heterocyclyl ring, wherein the dotted line between the two adjacent carbons represents a single bond, a double bond or an aromatic bond.

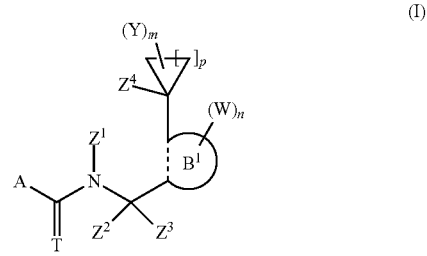

17 Claims, No Drawings

FUNGICIDAL N-CYCLOALKYL-N-{[ORTHO-(1-SUBSTITUTED-CYCLOALKYL)HETEROARYL]METHYL}(THIO)CARBOXAMIDES

CROSS REFERENCE TO RELATED APPLICATIONS

This application is the national stage of International Application No. PCT/EP2016/061203, filed internationally on May 19, 2016, which claims the benefit of European Application No. 15290134.4, filed May 21, 2015.

The present invention relates to fungicidal N-cycloalkyl-N-{[ortho-(1-substitutedcycloalkyl)heteroaryl]-methylene}carboxamide derivatives and their thiocarbonyl derivatives, their process of preparation and intermediate compounds for their preparation, their use as fungicides, particularly in the form of fungicidal compositions and methods for the control of phytopathogenic fungi of plants, using these compounds or their compositions.

In international patent application WO-2006/120224 certain N-cycloalkyl-N-(pyridylmethyl)carboxamides are generically embraced in a broad disclosure of numerous compounds of the following formula:

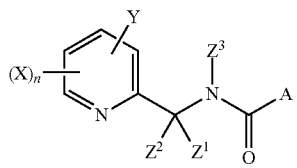

wherein A represents a carbo-linked, unsaturated, 5-membered heterocyclyl group, $Z^3$ represents a substituted or non-substituted $C_3$-$C_7$-cycloalkyl group, Y represents a haloalkyl group and X can represent various substituents among which an unsubstituted $C_3$-$C_7$-cycloalkyl. However, there is no explicit disclosure or suggestion to select in this document of any such derivative wherein X can represent a substituted $C_3$-$C_7$-cycloalkyl.

In international patent application WO-2008/015189 certain N-cycloalkyl-N-(heteroarylmethyl) (thio)carboxamides are generically embraced in a broad disclosure of numerous compounds of the following formula:

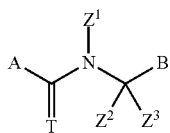

wherein A represents a carbo-linked, unsaturated, 5-membered heterocyclyl group, T can represent O or S, $Z^1$ represents a substituted or non-substituted $C_3$-$C_7$-cycloalkyl group, B represents a carbo-linked, unsaturated, 5-membered heterocyclyl group that can be substituted by up to four groups X, and X can represent various substituents among which an unsubstituted $C_3$-$C_7$-cycloalkyl. However, there is no explicit disclosure or suggestion to select in this document of any such derivative wherein X can represent a substituted $C_3$-$C_7$-cycloalkyl.

In international patent application WO-2008/037789 certain N-cycloalkyl-N-(heteroarylmethyl) (thio)carboxamides are generically embraced in a broad disclosure of numerous compounds of the following formula:

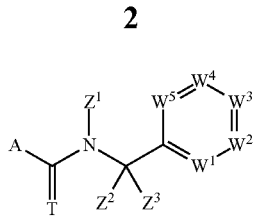

wherein A represents a carbo-linked, partially saturated or unsaturated, 5-membered heterocyclyl group, T can represent O or S, $Z^1$ represents a substituted or non-substituted $C_3$-$C_7$-cycloalkyl group, $W^1$ to $W^5$ can independently represent N or $CR^b$ and at least one $W^1$ to $W^5$ represents N, and $R^b$ can represent various substituents among which an unsubstituted $C_3$-$C_7$-cycloalkyl. However, there is no explicit disclosure or suggestion to select in this document of any such derivative wherein $R^b$ can represent a substituted $C_3$-$C_7$-cycloalkyl.

In international patent applications WO-2009/016221 and WO-2009/016222 certain N-cycloalkyl-N-(heteroarylmethyl)(thio)carboxamides are generically embraced in a broad disclosure of numerous compounds of the following formula:

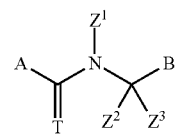

wherein A represents a carbo-linked, partially saturated or unsaturated, 5-membered heterocyclyl group, T can represent O or S, $Z^1$ represents a substituted or non-substituted $C_3$-$C_7$-cycloalkyl group, B can represent a carbo-linked, unsaturated, benzofused, 5- or 6-membered heterocyclyl group that can be substituted by at least a $R^{b1}$, $R^{b2}$ or $R^{b3}$ group, and $R^{b1}$, $R^{b2}$ or $R^{b3}$ can represent various substituents among which an unsubstituted $C_3$-$C_7$-cycloalkyl. However, there is no explicit disclosure or suggestion to select in this document of any such derivative wherein $R^{b1}$, $R^{b2}$ or $R^{b3}$ can represent a substituted $C_3$-$C_7$-cycloalkyl.

In international patent applications WO-2010/130767 certain N-cycloalkyl-N-(2-pyridylmethyl)(thio) carboxamides are generically embraced in a broad disclosure of numerous compounds of the following formula:

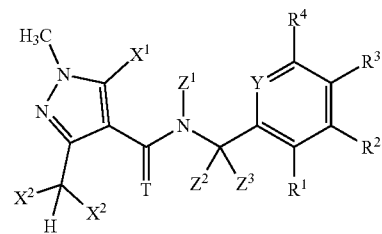

wherein $X^1$ and $X^2$ represent a fluorine of a chlorine atom, T can represent O or S, $Z^1$ represents a substituted or non-substituted cyclopropyl group or a substituted or non-substituted $C_4$-$C_7$-cycloalkyl group, Y can represent N and each substituent $R^i$, i being an integer from 1 to 4, can, independently, represent various substituents among which a substituted or unsubstituted $C_3$-$C_7$-cycloalkyl. However, there is no explicit disclosure or suggestion to select in this document of any such derivative wherein $R^1$ can represent a substituted $C_3$-$C_7$-cycloalkyl when Y represents N.

In international patent application WO-2012/059497 certain N-cycloalkyl-N-(heteroarylmethyl)(thio) carboxamides are generically embraced in a broad disclosure of numerous compounds of the following formula:

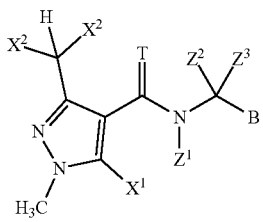

wherein $X^1$ and $X^2$ represent a fluorine of a chlorine atom, T can represent O or S, $Z^1$ represents a substituted or non-substituted $C_3$-$C_7$-cycloalkyl group, B can represent a saturated, partially saturated or unsaturated, monocyclic or fused bicyclic 4-, 5-, 6-, 7-, 8-, 9-, 10-membered ring that can be substituted by at least a X group, and X can represent various substituents among which a substituted or unsubstituted $C_3$-$C_7$-cycloalkyl. However, there is no explicit disclosure or suggestion to select in this document of any such derivative wherein X can represent a substituted $C_3$-$C_7$-cycloalkyl.

In international patent application WO-2014/172191 certain N-cycloalkyl-N-(heteroarylmethyl)(thio) carboxamides are generically embraced in a broad disclosure of numerous compounds of the following formula:

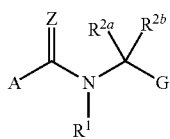

wherein A can represents various carbo-linked, partially saturated or unsaturated, 5- or 6-membered heterocyclyl groups, Z can represent O or S, $R^1$ can represent a substituted or non-substituted $C_3$-$C_5$-cycloalkyl group, G can represent a pyridinyl, pyridazinyl or pyrazinyl group optionally substituted by $R^3$, and $R^3$ can represent various substituents among which a unsubstituted $C_3$-$C_5$-cycloalkyl. However, there is no explicit disclosure or suggestion to select in this document of any such derivative wherein $R^3$ can represent a substituted $C_3$-$C_7$-cycloalkyl.

Accordingly, the present invention provides a N-cycloalkyl-N-{[ortho-(1-substitutedcycloalkyl)heteroaryl]-methylene}(thio)carboxamide of formula (I)

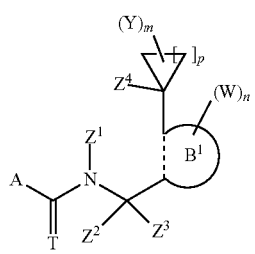

(I)

wherein

A represents a carbo-linked, unsaturated or partially saturated, 5-membered heterocyclyl group that can be substituted by up to four groups R that can be the same or different, provided that A does not represent a 3-(dihalogenomethyl)-5-halogeno-1-methyl-1H-pyrazol-4-yl group wherein the halogeno atoms can independently represent a fluoro or chloro atom;

T represents O or S;

n represents 0, 1, 2, 3 or 4;

m represents 0, 1, 2, 3, 4, 5 or 6;

p represents 1, 2, 3, 4 or 5;

$Z^1$ represents a non-substituted $C_3$-$C_7$-cycloalkyl or a $C_3$-$C_7$-cycloalkyl substituted by up to 10 atoms or groups that can be the same or different and that can be selected in the list consisting of halogen atoms, cyano, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl and di-$C_1$-$C_8$-alkylaminocarbonyl;

$Z^2$ and $Z^3$, which can be the same or different, represent a hydrogen atom; substituted or non-substituted $C_1$-$C_8$-alkyl; substituted or non-substituted $C_2$-$C_8$-alkenyl; substituted or non-substituted $C_2$-$C_8$-alkynyl; cyano; isonitrile; nitro; a halogen atom; substituted or non-substituted $C_1$-$C_8$-alkoxy; substituted or non-substituted $C_2$-$C_8$-alkenyloxy; substituted or non-substituted $C_2$-$C_8$-alkynyloxy; substituted or non-substituted $C_3$-$C_7$-cycloalkyl; substituted or non-substituted $C_1$-$C_8$-alkylsulfanyl; substituted or non-substituted $C_1$-$C_8$-alkylsulfonyl; substituted or non-substituted $C_1$-$C_8$-alkylsulfinyl; amino; substituted or non-substituted $C_1$-$C_8$-alkylamino; substituted or non-substituted di-$C_1$-$C_8$-alkylamino; substituted or non-substituted $C_1$-$C_8$-alkoxycarbonyl; substituted or non-substituted $C_1$-$C_8$-alkylcarbamoyl; substituted or non-substituted di-$C_1$-$C_8$-alkylcarbamoyl; or substituted or non-substituted N—$C_1$-$C_8$-alkyl-$C_1$-$C_8$-alkoxy-carbamoyl; or $Z^2$ and $Z^3$ together with the carbon atom to which they are linked can form a substituted or non-substituted $C_3$-$C_7$-cycloalkyl;

$Z^4$ represents a halogen atom; hydroxy; cyano; substituted or non-substituted $C_1$-$C_8$-alkyl; $C_1$-$C_8$-halogenoalkyl having 1 to 5 halogen atoms; substituted or non-substituted $C_2$-$C_8$-alkenyl; $C_2$-$C_8$-halogenoalkenyl having 1 to 5 halogen atoms; substituted or non-substituted $C_2$-$C_8$-alkynyl; $C_2$-$C_8$-halogenoalkynyl having 1 to 5 halogen atoms; substituted or non-substituted $C_1$-$C_8$-alkoxy; $C_1$-$C_8$-halogenoalkoxy having 1 to 5 halogen atoms; substituted or non-substituted $C_1$-$C_8$-alkylsulfanyl; formyl; substituted or non-substituted $C_1$-$C_8$-alkylcarbonyl; carboxy; or substituted or non-substituted $C_1$-$C_8$-alkoxycarbonyl;

$B^1$ represents a carbo-linked unsaturated, monocyclic or fused bicyclic 5-, 6-, 8-, 9-, 10-membered heterocyclyl ring comprising from 1 up to 4 heteroatoms selected in the list consisting of N, O, S; wherein the dotted line between the two adjacent carbons represents a single bond, a double bond or an aromatic bond, with the proviso that $B^1$ is not a 1,3-benzodioxolyl group.

W independently represents a halogen atom; nitro; cyano; isonitrile; hydroxy; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-halogenoalkyl having 1 to 9 halogen atoms; substituted or non-substituted $C_2$-$C_8$-alkenyl; $C_2$-$C_8$-halogenoalkenyl having 1 to 9 halogen atoms; substituted or non-substituted $C_2$-$C_8$-alkynyl; $C_2$-$C_8$-halogenoalkynyl having 1 to 9 halogen atoms; substituted or non-substituted $C_1$-$C_8$-alkoxy; $C_1$-$C_8$-halogenoalkoxy having 1 to 9 halogen atoms; substituted or non-substituted $C_1$-$C_8$-alkylsulfanyl; $C_1$-$C_8$-halogenoalkylsulfanyl having 1 to 9 halogen atoms; substituted or non-substituted $C_1$-$C_8$-alkylsulfinyl; $C_1$-$C_8$-halogenoalkylsulfinyl having 1 to 9 halogen atoms; substituted or non-substituted $C_1$-$C_8$-alkylsulfonyl; $C_1$-$C_8$-halogenoalkylsulfonyl having 1 to 9 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-halogenoalkenyloxy having 1 to 9 halogen atoms; substituted or non-substituted $C_3$-$C_8$-alkynyloxy; $C_2$-$C_8$-halogenoalkynyloxy having 1 to 9 halogen atoms; substituted or non-substituted $C_3$-$C_7$-cycloalkyl; $C_3$-$C_7$-halogenocycloalkyl having 1 to 9 halogen atoms; substituted or non-substituted ($C_3$-$C_7$-cycloalkyl)-$C_1$-$C_8$-alkyl; substituted or non-substituted $C_4$-$C_7$-cycloalkenyl; $C_4$-$C_7$-halogenocycloalkenyl having 1 to 9 halogen atoms; substituted or non-substituted ($C_3$-$C_7$-cycloalkyl)-$C_2$-$C_8$-alkenyl; substituted or non-substituted ($C_3$-$C_7$-cycloalkyl)-$C_2$-$C_8$-alkynyl; substituted or non-substituted bicyclo[2.2.1]heptanyl; substituted or non-substituted bicyclo[2.2.1]heptenyl; substituted or non-substituted tri($C_1$-$C_8$)alkylsilyl; substituted or non-substituted tri($C_1$-$C_8$)alkylsilyl-$C_1$-$C_8$-alkyl; substituted or non-substituted $C_1$-$C_8$-alkylcarbonyl; $C_1$-$C_8$-halogenoalkylcarbonyl having 1 to 9 halogen atoms; substituted or non-substituted $C_1$-$C_8$-alkylcarbonyloxy; $C_1$-$C_8$-halogenoalkylcarbonyloxy having 1 to 9 halogen atoms; substituted or non-substituted $C_1$-$C_8$-alkylcarbonylamino; $C_1$-$C_8$-halogenoalkylcarbonylamino having 1 to 9 halogen atoms; substituted or non-substituted $C_1$-$C_8$-alkoxycarbonyl; $C_1$-$C_8$-halogenoalkoxycarbonyl having 1 to 9 halogen atoms; substituted or non-substituted $C_1$-$C_8$-alkyloxycarbonyloxy; $C_1$-$C_8$-halogenoalkoxycarbonyloxy having 1 to 9 halogen atoms; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl that can be substituted by up to 6 groups Q which can be the same or different; $C_1$-$C_8$-arylalkyl that can be substituted by up to 6 groups Q which can be the same or different; $C_2$-$C_8$-arylalkenyl that can be substituted by up to 6 groups Q which can be the same or different; $C_2$-$C_8$-arylalkynyl that can be substituted by up to 6 groups Q which can be the same or different; aryloxy that can be substituted by up to 6 groups Q which can be the same or different; arylsulfanyl that can be substituted by up to 6 groups Q which can be the same or different; arylamino that can be substituted by up to 6 groups Q which can be the same or different; $C_1$-$C_8$-arylalkyloxy that can be substituted by up to 6 groups Q which can be the same or different; $C_1$-$C_8$-arylalkylsulfanyl that can be substituted by up to 6 groups Q which can be the same or different; $C_1$-$C_8$-arylalkylamino that can be substituted by up to 6 groups Q which can be the same or different; $C_1$-$C_8$-heteroarylalkyl that can be substituted by up to 6 groups Q which can be the same or different; heteroaryl which can be substituted by up to 4 groups Q; or heteroaryloxy which can be substituted by up to 4 groups Q;

Y independently represents a halogen atom; $C_1$-$C_8$-alkyl; $C_1$-$C_8$-halogenoalkyl having 1 to 9 halogen atoms; substituted or non-substituted $C_1$-$C_8$-alkoxy; $C_1$-$C_8$-halogenoalkoxy having 1 to 9 halogen atoms; substituted or non-substituted $C_1$-$C_8$-alkylsulfanyl; $C_1$-$C_8$-halogenoalkylsulfanyl having 1 to 9 halogen atoms; or substituted or non-substituted $C_1$-$C_8$-alkoxycarbonyl;

Q independently represents a halogen atom, cyano, nitro, substituted or non-substituted $C_1$-$C_8$-alkyl, $C_1$-$C_8$-halogenoalkyl comprising up to 9 halogen atoms that can be the same or different, substituted or non-substituted $C_1$-$C_8$-alkoxy, $C_1$-$C_8$-halogenoalkoxy comprising up to 9 halogen atoms that can be the same or different, substituted or non-substituted $C_1$-$C_8$-alkylsulfanyl, $C_1$-$C_8$-halogenoalkylsulfanyl comprising up to 9 halogen atoms that can be the same or different, substituted or non-substituted tri($C_1$-$C_8$)alkylsilyl, substituted or non-substituted tri($C_1$-$C_8$)alkylsilyl-$C_1$-$C_8$-alkyl, substituted or non-substituted ($C_1$-$C_8$-alkoxyimino)-$C_1$-$C_8$-alkyl, or substituted or non-substituted (benzyloxyimino)-$C_1$-$C_8$-alkyl;

R independently represents hydrogen atom; halogen atom; nitro; cyano; hydroxy; amino; sulfanyl; pentafluoro-$\lambda^6$-sulfanyl; substituted or non-substituted ($C_1$-$C_8$-alkoxyimino)-$C_1$-$C_8$-alkyl; substituted or non-substituted (benzyloxyimino)-$C_1$-$C_8$-alkyl; substituted or non-substituted $C_1$-$C_8$-alkyl; $C_1$-$C_8$-halogenoalkyl having 1 to 9 halogen atoms; substituted or non-substituted $C_2$-$C_8$-alkenyl; $C_2$-$C_8$-halogenoalkenyl having 1 to 9 halogen atoms; substituted or non-substituted $C_2$-$C_8$-alkynyl; $C_2$-$C_8$-halogenoalkynyl having 1 to 9 halogen atoms; substituted or non-substituted $C_1$-$C_8$-alkoxy; $C_1$-$C_8$-halogenoalkoxy having 1 to 9 halogen atoms; substituted or non-substituted $C_1$-$C_8$-alkylsulfanyl; $C_1$-$C_8$-halogenoalkylsulfanyl having 1 to 9 halogen atoms; substituted or non-substituted $C_1$-$C_8$-alkylsulfinyl; $C_1$-$C_8$-halogenoalkylsulfinyl having 1 to 9 halogen atoms; substituted or non-substituted $C_1$-$C_8$-alkylsulfonyl; $C_1$-$C_8$-halogenoalkylsulfonyl having 1 to 9 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; substituted or non-substituted $C_3$-$C_8$-alkynyloxy; substituted or non-substituted $C_3$-$C_7$-cycloalkyl; $C_3$-$C_7$-halogenocycloalkyl having 1 to 9 halogen atoms; substituted or non-substituted tri($C_1$-$C_8$)alkylsilyl; substituted or non-substituted $C_1$-$C_8$-alkylcarbonyl; $C_1$-$C_8$-halogenoalkylcarbonyl having 1 to 9 halogen atoms; substituted or non-substituted $C_1$-$C_8$-alkoxycarbonyl; $C_1$-$C_8$-halogenoalkoxycarbonyl having 1 to 9 halogen atoms; substituted or non-substituted $C_1$-$C_8$-alkylcarbamoyl; substituted or non-substituted di-$C_1$-$C_8$-alkylcarbamoyl;

phenoxy; phenylsulfanyl; phenylamino; benzyloxy; benzylsulfanyl; or benzylamino;

as well as its salts, N-oxides, metal complexes, metalloid complexes and optically active isomers or geometric isomers thereof.

Unless indicated otherwise, a group or a substituent that is substituted according to the invention can be substituted by one or more of the following groups or atoms: a halogen atom; nitro; hydroxyl; cyano; isonitrile; amino; sulfanyl; a pentafluoro-$\lambda^6$-sulfanyl group; formyl; formyloxy; formylamino; carbamoyl; N-hydroxycarbamoyl; carbamate; (hydroxyimino)-$C_1$-$C_8$-alkyl; $C_1$-$C_8$-alkyl; a tri($C_1$-$C_8$-alkyl) silyl; $C_3$-$C_8$-cycloalkyl; $C_1$-$C_8$-halogenoalkyl having 1 to 5 halogen atoms; a $C_3$-$C_8$-halogenocycloalkyl having 1 to 5 halogen atoms; $C_2$-$C_8$-alkenyl; $C_2$-$C_8$-alkynyl; $C_2$-$C_8$-alkenyloxy; $C_2$-$C_8$-alkynyloxy; $C_1$-$C_8$-alkylamino; di-$C_1$-$C_8$-alkylamino; $C_1$-$C_8$-alkoxy; $C_1$-$C_8$-halogenoalkoxy having 1 to 5 halogen atoms; $C_1$-$C_8$-alkylsulfanyl; $C_1$-$C_8$-halogenoalkylsulfanyl having 1 to 5 halogen atoms; $C_2$-$C_8$-alkenyloxy; $C_2$-$C_8$-halogenoalkenyloxy having 1 to 5 halogen atoms; $C_3$-$C_8$-alkynyloxy; $C_3$-$C_8$-halogenoalkynyloxy having 1 to 5 halogen atoms; $C_1$-$C_8$-alkylcarbonyl; $C_1$-$C_8$-halogenoalkylcarbonyl having 1 to 5 halogen atoms; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$-alkoxycarbamoyl; $C_1$-$C_8$-alkoxycarbonyl; $C_1$-$C_8$-halogenoalkoxycarbonyl having 1 to 5 halogen atoms; $C_1$-$C_8$-alkylcarbonyloxy; $C_1$-$C_8$-halogenoalkylcarbonyloxy having 1 to 5 halogen atoms; $C_1$-$C_8$-alkylcarbonylamino; $C_1$-$C_8$-halogenoalkylcarbonylamino having 1 to 5 halogen atoms; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkylsulfanyl; $C_1$-$C_8$-halogenoalkylsulfanyl having 1 to 5 halogen atoms; $C_1$-$C_8$-alkylsulfinyl; $C_1$-$C_8$-halogenoalkylsulfinyl having 1 to 5 halogen atoms; $C_1$-$C_8$-alkylsulfonyl; $C_1$-$C_8$-halogenoalkylsulfonyl having 1 to 5 halogen atoms; $C_1$-$C_8$-alkylaminosulfamoyl; di-$C_1$-$C_8$-alkylaminosulfamoyl; ($C_1$-$C_8$-alkoxyimino)-$C_1$-$C_6$-alkyl; ($C_1$-$C_6$-alkenyloxyimino)-$C_1$-$C_6$-alkyl; ($C_1$-$C_6$-alkynyloxyimino)-$C_1$-$C_6$-alkyl; 2-oxopyrrolidin-1-yl; (benzyloxyimino)-$C_1$-$C_8$-alkyl; $C_1$-$C_8$-alkoxyalkyl; $C_1$-$C_8$-halogenoalkoxyalkyl having 1 to 5 halogen atoms; benzyloxy; benzylsulfanyl; benzylamino; aryloxy; arylsulfanyl or arylamino.

According to the invention, the following generic terms are generally used with the following meanings:
halogen means fluorine, chlorine, bromine or iodine,
carboxy means —C(=O)OH;
carbonyl means —C(=O)—;
carbamoyl means —C(=O)NH$_2$;
N-hydroxycarbamoyl means —C(=O)NHOH;
SO represents a sulfoxide group;
SO$_2$ represents a sulfone group;
heteroatom means sulfur, nitrogen or oxygen;
methylene means the diradical —CH$_2$—;
an alkyl group, an alkenyl group and an alkynyl group as well as moieties containing these terms, can be linear or branched;
halogenated groups, notably haloalkyl, haloalkoxy and cycloalkyl groups, can comprise up to nine identical or different halogen atoms;
the term "aryl" means phenyl or naphthyl;
the term "heteroaryl" means a saturated, partially saturated or unsaturated, monocyclic or fused bicyclic 3-, 4-, 5-, 6-, 7-, 8-, 9-, 10-membered ring comprising from 1 up to 4 heteroatoms selected in the list consisting of N, O and S.

In the case of an amino group or the amino moiety of any other amino-containing group, substituted by two substituents that can be the same or different, the two substituents together with the nitrogen atom to which they are linked can form a heterocyclyl group, preferably a 5- to 7-membered heterocyclyl group, that can be substituted or that can include other hetero atoms, for example a morpholino group or piperidinyl group.

Where a compound of the invention can be present in tautomeric form, such a compound is understood hereinabove and hereinbelow also to include, where applicable, corresponding tautomeric forms, even when these are not specifically mentioned in each case.

Any of the compounds of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions) and to the mixtures of all the possible stereoisomers, in all proportions. The diastereoisomers and/or the optical isomers can be separated according to the methods which are known per se by the man ordinary skilled in the art.

Any of the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

Any of the compounds of the present invention can also exist in one or more geometric isomer forms depending on the relative position (syn/anti or cis/trans or endo/exo) of the substituents of the chain or ring. The invention thus relates equally to all syn/anti (or cis/trans or endo/exo) isomers and to all possible syn/anti (or cis/trans or endo/exo) mixtures, in all proportions. The syn/anti (or cis/trans or endo/exo) isomers can be separated according to general methods, which are known per se by the man ordinary skilled in the art.

Preferred compounds according to the invention are compounds of formula (I) wherein A is selected in the list consisting of:

a heterocycle of formula (A$^1$)

(A$^1$)

wherein:

R$^1$ to R$^3$ that can be the same or different represent a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or $C_1$-$C_5$-halogenoalkoxy comprising up to 9 halogen atoms that can be the same or different;

a heterocycle of formula (A²)

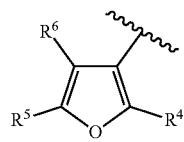

wherein:

R⁴ to R⁶ that can be the same or different represent a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or $C_1$-$C_5$-halogenoalkoxy comprising up to 9 halogen atoms that can be the same or different;

a heterocycle of formula (A³)

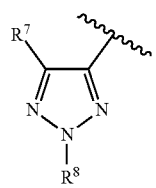

wherein:

R⁷ represents a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or $C_1$-$C_5$-halogenoalkoxy comprising up to 9 halogen atoms that can be the same or different;

R⁸ represents a hydrogen atom or a substituted or non-substituted $C_1$-$C_5$-alkyl;

a heterocycle of formula (A⁴)

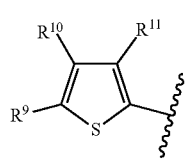

wherein:

R⁹ to R¹¹ that can be the same or different represent a hydrogen atom; a halogen atom; substituted or non-substituted $C_1$-$C_5$-alkyl; amino; substituted or non-substituted $C_1$-$C_5$-alkoxy; substituted or non-substituted $C_1$-$C_5$-alkylsulfanyl; $C_1$-$C_5$-halogenoalkyl comprising up to 9 halogen atoms that can be the same or different or $C_1$-$C_5$-halogenoalkoxy comprising up to 9 halogen atoms that can be the same or different;

a heterocycle of formula (A⁵)

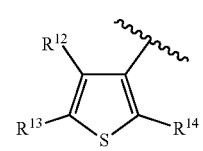

wherein:

R¹² and R¹³ that can be the same or different represent a hydrogen atom; a halogen atom; substituted or non-substituted $C_1$-$C_5$-alkyl; substituted or non-substituted $C_1$-$C_5$-alkoxy; amino; $C_1$-$C_5$-halogenoalkyl comprising up to 9 halogen atoms that can be the same or different or $C_1$-$C_5$-halogenoalkoxy comprising up to 9 halogen atoms that can be the same or different;

R¹⁴ represents a hydrogen atom; a halogen atom; substituted or non-substituted $C_1$-$C_5$-alkyl; substituted or non-substituted $C_1$-$C_5$-alkoxy; amino; $C_1$-$C_5$-halogenoalkyl comprising up to 9 halogen atoms that can be the same or different or $C_1$-$C_5$-halogenoalkoxy comprising up to 9 halogen atoms that can be the same or different;

a heterocycle of formula (A⁶)

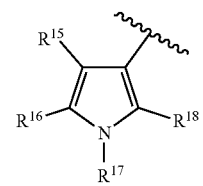

wherein:

R¹⁵ represents a hydrogen atom; a halogen atom; a cyano; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

R¹⁶ and R¹⁸ that can be the same or different represent a hydrogen atom; a halogen atom; substituted or non-substituted $C_1$-$C_5$-alkoxycarbonyl; substituted or non-substituted $C_1$-$C_5$-alkyl; $C_1$-$C_5$-halogenoalkoxy comprising up to 9 halogen atoms that can be the same or different or $C_1$-$C_5$-halogenoalkyl comprising up to 9 halogen atoms that can be the same or different;

R¹⁷ represent a hydrogen atom or substituted or non-substituted $C_1$-$C_5$-alkyl;

a heterocycle of formula (A⁷)

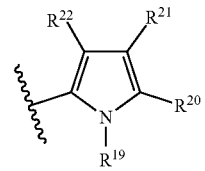

wherein:

R¹⁹ represents a hydrogen atom or a $C_1$-$C_5$-alkyl

R²⁰ to R²² that can be the same or different represent a hydrogen atom; a halogen atom; substituted or non-substituted C$_1$-C$_5$-alkyl or C$_1$-C$_5$-halogenoalkyl comprising up to 9 halogen atoms that can be the same or different;

a heterocycle of formula (A$^8$)

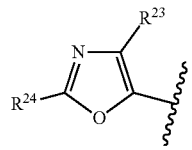

(A$^8$)

wherein:

R$^{23}$ represents a hydrogen atom; a halogen atom; substituted or non-substituted C$_1$-C$_5$-alkyl or C$_1$-C$_5$-halogenoalkyl comprising up to 9 halogen atoms that can be the same or different;

R$^{24}$ represents a hydrogen atom or substituted or non-substituted C$_1$-C$_6$-alkyl or C$_1$-C$_6$-halogenoalkyl comprising up to 9 halogen atoms that can be the same or different;

a heterocycle of formula (A$^9$)

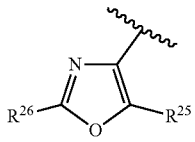

(A$^9$)

wherein:

R$^{25}$ represents a hydrogen atom; a halogen atom; substituted or non-substituted C$_1$-C$_5$-alkyl or C$_1$-C$_5$-halogenoalkyl comprising up to 9 halogen atoms that can be the same or different;

R$^{26}$ represents a hydrogen atom; substituted or non-substituted C$_1$-C$_5$-alkyl or C$_1$-C$_5$-halogenoalkyl comprising up to 9 halogen atoms that can be the same or different;

a heterocycle of formula (A$^{10}$)

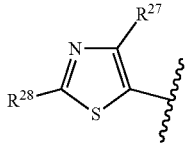

(A$^{10}$)

wherein:

R$^{27}$ represents a hydrogen atom; a halogen atom; substituted or non-substituted C$_1$-C$_5$-alkyl or C$_1$-C$_5$-halogenoalkyl comprising up to 9 halogen atoms that can be the same or different;

R$^{28}$ represents a hydrogen atom; a halogen atom; substituted or non-substituted C$_1$-C$_5$-alkyl; C$_1$-C$_5$-halogenoalkyl comprising up to 9 halogen atoms that can be the same or different; C$_1$-C$_5$-halogenoalkoxy comprising up to 9 halogen atoms that can be the same or different; amino; substituted or non-substituted C$_1$-C$_5$-alkylamino or substituted or non-substituted di(C$_1$-C$_5$-alkyl)amino;

a heterocycle of formula (A$^{11}$)

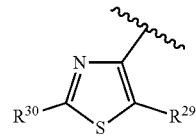

(A$^{11}$)

wherein:

R$^{29}$ represents a hydrogen atom; a halogen atom; substituted or non-substituted C$_1$-C$_5$-alkyl; substituted or non-substituted C$_1$-C$_5$-alkoxy; C$_1$-C$_5$-halogenoalkoxy comprising up to 9 halogen atoms that can be the same or different or C$_1$-C$_5$-halogenoalkyl comprising up to 9 halogen atoms that can be the same or different;

R$^{30}$ represents a hydrogen atom; a halogen atom; substituted or non-substituted C$_1$-C$_5$-alkyl; C$_1$-C$_5$-halogenoalkyl comprising up to 9 halogen atoms that can be the same or different; C$_1$-C$_5$-halogenoalkoxy comprising up to 9 halogen atoms that can be the same or different; amino; substituted or non-substituted C$_1$-C$_5$-alkylamino or substituted or non-substituted di(C$_1$-C$_5$-alkyl)amino;

a heterocycle of formula (A$^{12}$)

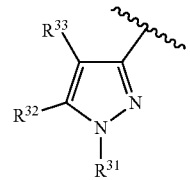

(A$^{12}$)

wherein:

R$^{31}$ represents a hydrogen atom or a substituted or non-substituted C$_1$-C$_5$-alkyl R$^{32}$ represents a hydrogen atom; a halogen atom; substituted or non-substituted C$_1$-C$_5$-alkyl or C$_1$-C$_5$-halogenoalkyl comprising up to 9 halogen atoms that can be the same or different;

R$^{33}$ represents a hydrogen atom; a halogen atom; a nitro; substituted or non-substituted C$_1$-C$_5$-alkyl; substituted or non-substituted C$_1$-C$_5$-alkoxy; C$_1$-C$_5$-halogenoalkoxy comprising up to 9 halogen atoms that can be the same or different or C$_1$-C$_5$-halogenoalkyl comprising up to 9 halogen atoms that can be the same or different;

a heterocycle of formula (A$^{13}$)

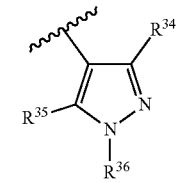

(A$^{13}$)

wherein:

R$^{34}$ represents a hydrogen atom; a halogen atom; substituted or non-substituted C$_1$-C$_5$-alkyl; substituted or non-substituted C$_3$-C$_5$-cycloalkyl; C$_1$-C$_5$-halogenoalkyl comprising up to 9 halogen atoms that can be the same or different; substituted or non-substituted C$_1$-C$_5$-alkoxy; substituted or non-substituted $C_2$-$C_5$-alkynyloxy or $C_1$-$C_5$-halogenoalkoxy comprising up to 9 halogen atoms that can be the same or different;

$R^{35}$ represents a hydrogen atom; a halogen atom; substituted or non-substituted $C_1$-$C_5$-alkyl; a cyano; substituted or non-substituted $C_1$-$C_5$-alkoxy; substituted or non-substituted $C_1$-$C_5$-alkylsulfanyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or substituted or non-substituted di($C_1$-$C_5$-alkyl)amino;

$R^{36}$ represents a hydrogen atom or substituted or non-substituted $C_1$-$C_5$-alkyl; provided that $R^{35}$ does not represent a fluoro or a chloro atom when $R^{34}$ simultaneously represents a difluoromethyl or a dichloromethyl group and $R^{36}$ simultaneously represents a methyl group;

a heterocycle of formula ($A^{14}$)

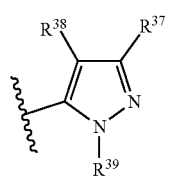

(A$^{14}$)

wherein:
$R^{37}$ and $R^{38}$ that can be the same or different represent a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or a substituted or non-substituted $C_1$-$C_5$-alkylsulfanyl;

$R^{39}$ represents a hydrogen atom or substituted or non-substituted $C_1$-$C_5$-alkyl;

a heterocycle of formula ($A^{15}$)

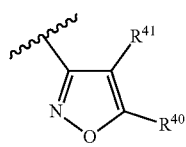

(A$^{15}$)

wherein:
$R^{40}$ and $R^{41}$ that can be the same or different represent a hydrogen atom; a halogen atom; substituted or non-substituted $C_1$-$C_5$-alkyl or $C_1$-$C_5$-halogenoalkyl comprising up to 9 halogen atoms that can be the same or different;

a heterocycle of formula ($A^{16}$)

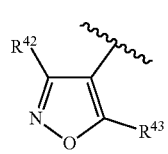

(A$^{16}$)

wherein:
$R^{42}$ and $R^{43}$ that can be the same or different represent a hydrogen atom; a halogen atom; substituted or non-substituted $C_1$-$C_5$-alkyl; $C_1$-$C_5$-halogenoalkyl comprising up to 9 halogen atoms that can be the same or different or amino;

a heterocycle of formula ($A^{17}$)

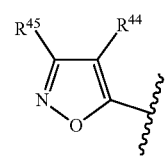

(A$^{17}$)

wherein:
$R^{44}$ and $R^{45}$ that can be the same or different represent a hydrogen atom; a halogen atom; substituted or non-substituted $C_1$-$C_5$-alkyl or $C_1$-$C_5$-halogenoalkyl comprising up to 9 halogen atoms that can be the same or different;

a heterocycle of formula ($A^{18}$)

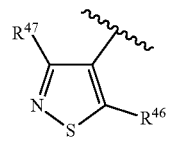

(A$^{18}$)

wherein:
$R^{47}$ represents a hydrogen atom; a halogen atom; substituted or non-substituted $C_1$-$C_5$-alkyl or $C_1$-$C_5$-halogenoalkyl comprising up to 9 halogen atoms that can be the same or different;

$R^{46}$ represents a hydrogen atom; a halogen atom; substituted or non-substituted $C_1$-$C_6$-alkyl; $C_1$-$C_6$-halogenoalkyl comprising up to 9 halogen atoms that can be the same or different or substituted or non-substituted $C_1$-$C_5$-alkylsulfanyl;

a heterocycle of formula ($A^{19}$)

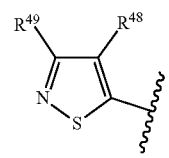

(A$^{19}$)

wherein:
$R^{49}$ and $R^{48}$ that can be the same or different represent a hydrogen atom; a halogen atom; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

a heterocycle of formula ($A^{20}$)

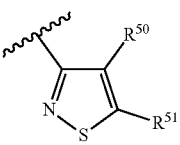

(A$^{20}$)

wherein:

$R^{50}$ and $R^{51}$ that can be the same or different represent a hydrogen atom; a halogen atom; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

a heterocycle of formula ($A^{21}$)

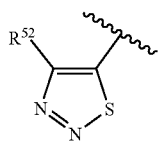

wherein:

$R^{52}$ represents a hydrogen atom; a halogen atom; substituted or non-substituted $C_1$-$C_5$-alkyl or $C_1$-$C_5$-halogenoalkyl comprising up to 9 halogen atoms that can be the same or different.

a heterocycle of formula ($A^{22}$)

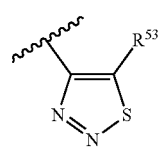

wherein:

$R^{53}$ represents a hydrogen atom; a halogen atom; substituted or non-substituted $C_1$-$C_5$-alkyl or $C_1$-$C_5$-halogenoalkyl comprising up to 9 halogen atoms that can be the same or different.

a heterocycle of formula ($A^{23}$)

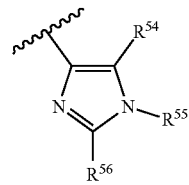

wherein:

$R^{54}$ and $R^{56}$ that can be the same or different represent a hydrogen atom; a halogen atom; substituted or non-substituted $C_1$-$C_5$-alkyl or $C_1$-$C_5$-halogenoalkyl comprising up to 9 halogen atoms that can be the same or different;

$R^{55}$ represents a hydrogen atom or substituted or non-substituted $C_1$-$C_5$-alkyl;

a heterocycle of formula ($A^{24}$)

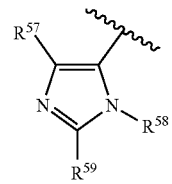

wherein:

$R^{57}$ and $R^{59}$ that can be the same or different represent a hydrogen atom; a halogen atom; substituted or non-substituted $C_1$-$C_5$-alkyl or $C_1$-$C_5$-halogenoalkyl comprising up to 9 halogen atoms that can be the same or different;

$R^{58}$ represents a hydrogen atom or substituted or non-substituted $C_1$-$C_5$-alkyl;

a heterocycle of formula ($A^{25}$)

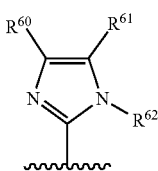

wherein:

$R^{60}$ and $R^{61}$ that can be the same or different represent a hydrogen atom; a halogen atom; substituted or non-substituted $C_1$-$C_3$-alkyl or $C_1$-$C_5$-halogenoalkyl comprising up to 9 halogen atoms that can be the same or different;

$R^{62}$ represents a hydrogen atom or substituted or non-substituted $C_1$-$C_5$-alkyl;

a heterocycle of formula ($A^{26}$)

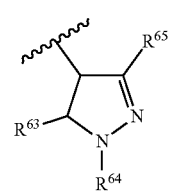

wherein:

$R^{65}$ represents a hydrogen atom; a halogen atom; substituted or non-substituted $C_1$-$C_5$-alkyl; substituted or non-substituted $C_3$-$C_5$-cycloalkyl; $C_1$-$C_5$-halogenoalkyl comprising up to 9 halogen atoms that can be the same or different; substituted or non-substituted $C_1$-$C_5$-alkoxy; substituted or non-substituted $C_2$-$C_5$-alkynyloxy or $C_1$-$C_5$-halogenoalkoxy comprising up to 9 halogen atoms that can be the same or different;

$R^{63}$ represents a hydrogen atom; a halogen atom; substituted or non-substituted $C_1$-$C_5$-alkyl; a cyano; substituted or non-substituted $C_1$-$C_5$-alkoxy; substituted or non-substituted $C_1$-$C_5$-alkylsulfanyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or di($C_1$-$C_5$-alkyl)amino;

$R^{64}$ represents a hydrogen atom or substituted or non-substituted $C_1$-$C_5$-alkyl.

More preferred compounds according to the invention are compounds of formula (I) wherein A is selected in the list consisting of $A^2$; $A^5$; $A^6$; $A^{10}$ and $A^{13}$ as herein-defined.

Even more preferred compounds according to the invention are compounds of formula (I) wherein A represents $A^{13}$ wherein $R^{34}$ represents a substituted or non-substituted $C_1$-$C_5$-alkyl, $C_1$-$C_5$-halogenoalkyl comprising up to 9 halogen atoms that can be the same or different; substituted or non-substituted $C_1$-$C_5$-alkoxy; $R^{35}$ represents a hydrogen atom or a halogen atom and $R^{36}$ represents a substituted or non-substituted $C_1$-$C_5$-alkyl.

Even more preferred compounds according to the invention are compounds of formula (I) wherein A represents $A^{13}$ wherein $R^{34}$ represents $C_1$-$C_5$-alkyl, or $C_1$-$C_5$-halogenoalkyl comprising up to 3 halogen atoms that can be the same or different; $R^{35}$ represents a hydrogen atom; a chlorine atom; or a fluorine atom; and $R^{36}$ represents $C_1$-$C_5$-alkyl, preferably a methyl.

Other preferred compounds according to the invention are compounds of formula (I) wherein T represents O.

Other preferred compounds according to the invention are compounds of formula (I) wherein $Z^1$ represents a substituted or non-substituted cyclopropyl.

Other more preferred compounds according to the invention are compounds of formula (I) wherein $Z^1$ represents a non-substituted cyclopropyl or a cyclopropyl substituted by 1 or 2 $C_1$-$C_5$-alkyl;

Other more preferred compounds according to the invention are compounds of formula (I) wherein $Z^1$ represents a non-substituted cyclopropyl or a 2-$C_1$-$C_5$-alkylcyclopropyl.

Other even more preferred compounds according to the invention are compounds of formula (I) wherein $Z^1$ represents a non-substituted cyclopropyl.

Other even more preferred compounds according to the invention are compounds of formula (I) wherein $Z^1$ represents a 2-methylcyclopropyl.

Other preferred compounds according to the invention are compounds of formula (I) wherein $Z^2$ and $Z^3$ independently represent a hydrogen atom or a methyl.

Other more preferred compounds according to the invention are compounds of formula (I) wherein $Z^2$ represents a hydrogen atom and $Z^3$ represents a hydrogen atom or a methyl.

Other more preferred compounds according to the invention are compounds of formula (I) wherein $Z^2$ and $Z^3$ represent a hydrogen atom.

Other preferred compounds according to the invention are compounds of formula (I) wherein n represents 0, 1 or 2, even preferred 0 or 1

Other preferred compounds according to the invention are compounds of formula (I) wherein m represents 0, 1, 2, 3 or 4, even preferred 0, 1 or 2, even more preferred 0.

Other preferred compounds according to the invention are compounds of formula (I) wherein p represents 1, 3 or 4, even more preferred 1.

Other preferred compounds according to the invention are compounds of formula (I) wherein $Z^4$ represents a halogen, non-substituted $C_1$-$C_4$-alkyl, $C_1$-$C_4$-halogenoalkyl having 1 to 3 halogen atoms, non-substituted $C_1$-$C_4$-alkyloxy, $C_1$-$C_4$-halogenoalkyloxy having 1 to 3 halogen atoms, substituted or non-substituted cyclopropyl, substituted or non-substituted $C_2$-$C_4$-alkenyl or substituted or non-substituted $C_2$-$C_4$-alkynyl.

Other preferred compounds according to the invention are compounds of formula (I) wherein $Z^4$ represents a halogen, non-substituted $C_1$-$C_4$-alkyl, $C_1$-$C_4$-halogenoalkyl having 1 to 3 halogen atoms, non-substituted $C_1$-$C_4$-alkyloxy, or $C_1$-$C_4$-halogenoalkyloxy having 1 to 3 halogen atoms;

Other preferred compounds according to the invention are compounds of formula (I) wherein $Z^4$ represents a halogen, non-substituted $C_1$-$C_4$-alkyl or non-substituted $C_1$-$C_4$-alkyloxy, particularly a halogen or non-substituted $C_1$-$C_4$-alkyl Other more preferred compounds according to the invention are compounds of formula (I) wherein $Z^4$ represents chloro, methyl or methoxy, particularly chloro or methyl.

Other preferred compounds according to the invention are compounds of formula (I) wherein $B^1$ represents a thienyl ring; a benzothiophenyl ring; a pyridinyl ring; a furanyl ring; or a benzofuranyl ring.

Other more preferred compounds according to the invention are compounds of formula (I) wherein $B^1$ represents a substituted or non-substituted thienyl ring.

Other more preferred compounds according to the invention are compounds of formula (I) wherein $B^1$ represents a substituted or non-substituted pyridinyl ring.

According to formula (I), $B^1$ is substituted by (W)n wherein W and n are herein defined.

Other preferred compounds according to the invention are compounds of formula (I) wherein preferences in $B^1$ as herein defined are combined with preferences of W and n as herein defined.

Other preferred compounds according to the invention are compounds of formula (I) wherein W independently, represents a halogen atom; non-substituted $C_1$-$C_8$-alkyl; $C_1$-$C_8$-halogenoalkyl comprising up to 9 halogen atoms which can be the same or different; substituted or non-substituted $C_2$-$C_8$-alkenyl; substituted or non-substituted $C_5$-$C_7$-cycloalkenyl; substituted or non-substituted $C_3$-$C_7$-cycloalkyl; tri($C_1$-$C_8$-alkyl)silyl; substituted or non-substituted $C_1$-$C_8$-alkoxy; or substituted or non-substituted $C_1$-$C_8$-alkylsulfanyl.

Other preferred compounds according to the invention are compounds of formula (I) wherein W independently, represents a halogen atom, non-substituted $C_1$-$C_8$-alkyl, or $C_1$-$C_8$-halogenoalkyl comprising up to 9 halogen atoms which can be the same or different.

Other preferred compounds according to the invention are compounds of formula (I) wherein W independently, represents a halogen atom, or non-substituted $C_1$-$C_8$-alkyl;

Other preferred compounds according to the invention are compounds of formula (I) wherein W independently, represents a chloro atom, a bromo atom or methyl.

Other preferred compounds according to the invention are compounds of formula (I) wherein Y independently, represents a halogen or a substituted or non-substituted $C_1$-$C_8$-alkyl, particularly a halogen or a non-substituted $C_1$-$C_8$-alkyl.

The above mentioned preferences with regard to the substituents of the compounds according to the invention can be combined in various manners. These combinations of preferred features thus provide sub-classes of compounds according to the invention. Examples of such sub-classes of preferred compounds according to the invention are:

preferred features of A with preferred features of T, $Z^1$ to $Z^4$, n, m, p, $B^1$, W and Y;

preferred features of T with preferred features of A, $Z^1$ to $Z^4$, n, m, p, $B^1$, W and Y;

preferred features of $Z^1$ with preferred features of A, T, $Z^2$ to $Z^4$, n, m, p, $B^1$, W and Y;

preferred features of $Z^2$ with preferred features of A, T, $Z^1$, $Z^3$ to $Z^4$, n, m, p, $B^1$, W and Y;

preferred features of $Z^3$ with preferred features of A, T, $Z^1$ to $Z^2$, $Z^4$, n, m, p, $B^1$, W and Y;

preferred features of $Z^4$ with preferred features of A, T, $Z^1$ to $Z^3$, n, m, p, $B^1$, W and Y;

preferred features of n with preferred features of A, T, $Z^1$ to $Z^4$, m, p, $B^1$, W and Y;

preferred features of m with preferred features of A, T, $Z^1$ to $Z^4$, n, p, $B^1$, W and Y;

preferred features of p with preferred features of A, T, $Z^1$ to $Z^4$, n, m, $B^1$, W and Y;

preferred features of $B^1$ with preferred features of A, T, $Z^1$ to $Z^4$, n, m, p, W and Y;

preferred features of W with preferred features of A, T, $Z^1$ to $Z^4$, n, m, p, $B^1$ and Y;

preferred features of Y with preferred features of A, T, $Z^1$ to $Z^4$, n, m, p, $B^1$ and W.

In these combinations of preferred features of the substituents of the compounds according to the invention, the said preferred features can also be selected among the more preferred features of each of A, T, $Z^1$ to $Z^4$, n, m, p, $B^1$, W and Y so as to form most preferred subclasses of compounds according to the invention.

In a particular embodiment of the invention, the following preferred features are combined:

$X^1$ is a fluorine atom;

$X^2$ is a chlorine or a fluorine atom; particularly a fluorine atom;

T represents O or S; particularly O;

$Z^1$ represents a non-substituted cyclopropyl or a cyclopropyl substituted by 1 or 2 $C_1$-$C_5$-alkyl; particularly a non-substituted cyclopropyl or a 2-$C_1$-$C_5$-alkylcyclopropyl; even more particularly a non-substituted cyclopropyl or a 2-methylcyclopropyl; —$Z^2$ and $Z^3$ independently represent a hydrogen atom or a methyl; particularly $Z^2$ represents a hydrogen atom and $Z^3$ represents a hydrogen atom or a methyl; even more particularly $Z^2$ and $Z^3$ represent a hydrogen atom;

n represents 0, 1 or 2; particularly 0 or 1;

m represents 0, 1, 2, 3 or 4; particularly 0, 1 or 2; even particularly 0;

p represents 1, 3 or 4; particularly 1;

$Z^4$ represents a halogen, non-substituted $C_1$-$C_4$-alkyl, $C_1$-$C_4$-halogenoalkyl having 1 to 3 halogen atoms, non-substituted $C_1$-$C_4$-alkyloxy, $C_1$-$C_4$-halogenoalkyloxy having 1 to 3 halogen atoms, substituted or non-substituted cyclopropyl, substituted or non-substituted $C_2$-$C_4$-alkenyl or substituted or non-substituted $C_2$-$C_4$-alkynyl; particularly a halogen, non-substituted $C_1$-$C_4$-alkyl or non-substituted $C_1$-$C_4$-alkyloxy; even more particularly a halogen or non-substituted $C_1$-$C_4$-alkyl, and even more particularly chloro or methyl;

$B^1$ represents a thienyl ring; a benzothiophenyl ring; a pyridinyl ring; a furanyl ring; or a benzofuranyl ring; particularly a thienyl or pyridinyl ring;

W independently represents a halogen atom, non-substituted $C_1$-$C_8$-alkyl, or $C_1$-$C_8$-halogenoalkyl comprising up to 9 halogen atoms which can be the same or different; particularly a halogen atom or non-substituted $C_1$-$C_8$-alkyl; even more particularly a chloro atom, a bromo atom or methyl;

Y independently represents a halogen or a substituted or non-substituted $C_1$-$C_8$-alkyl; particularly a halogen or a non-substituted $C_1$-$C_8$-alkyl The present invention also relates to a process for the preparation of the compound of formula (I). Thus, according to a further aspect of the present invention there is provided a process P1 for the preparation of a compound of formula (I) as herein-defined and wherein T represents O and that comprises reaction of an amine of formula (II) or one of its salts:

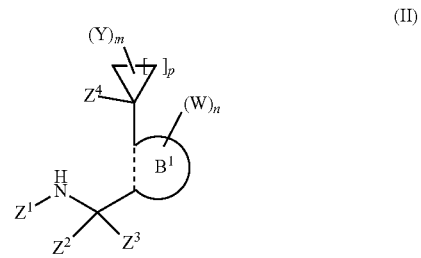

(II)

wherein $Z^1$, $Z^2$, $Z^3$, $Z^4$, n, m, p, $B^1$, W and Y are as herein-defined; with a carboxylic acid derivative of formula (III):

(III)

wherein A is as herein-defined and $U^1$ represents a leaving group selected in the list consisting of a halogen atom, a hydroxyl group, —$OR^a$, —$OC(=O)R^a$, $R^a$ being a substituted or non-substituted $C_1$-$C_6$-alkyl, a substituted or non-substituted $C_1$-$C_6$-haloalkyl, a benzyl, 4-methoxybenzyl or pentafluorophenyl group; in the presence, if necessary, of a catalyst and in the presence of a condensing agent in case $U^1$ represents a hydroxyl group, and in the presence of an acid binder in case $U^1$ represents a halogen atom.

N-substituted amine derivatives of formula (II) are known or can be prepared by known processes such as reductive amination of aldehydes of formula (IV):

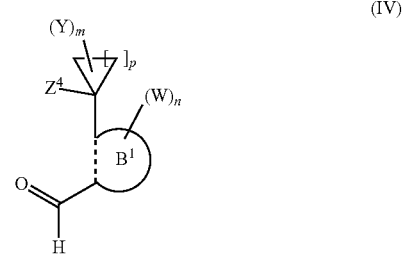

(IV)

wherein $Z^4$, n, m, p, $B^1$, W and Y are as herein-defined, or reductive amination of ketones (*Bioorganics and Medicinal Chemistry Letters* (2006), 16, 2014), or reduction of imines (*Tetrahedron* (2005), 61, 11689), or nucleophilic substitution by an amine of halogenomethylheterocyclic derivatives of formula (Va):

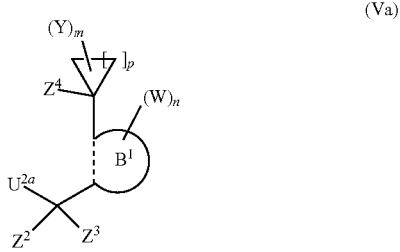

(Va)

wherein $U^{2a}$ is a halogen, preferentially chloro, bromo and iodo, and $Z^4$, n, m, p, $B^1$, W and Y are as herein-defined, or nucleophilic substitution by an amine of (aryl- or alkyl-sulfonyloxy)methylheterocyclic derivatives of formula (Vb):

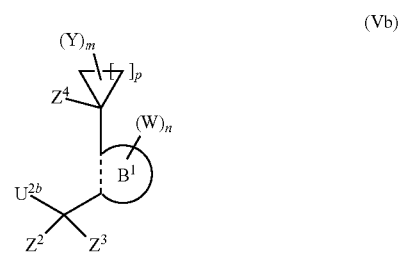

(Vb)

wherein $U^{2b}$ is an arylsulfonate or alkylsulfonate, preferentially tosylate or mesylate, and $Z^4$, n, m, p, $B^1$, W and Y are as herein-defined (*Journal of Medicinal Chemistry* (2002), 45, 3887).

Compounds of formula (Vb) wherein $Z^2$ and $Z^3$ are hydrogen and $U^{2b}$, $Z^4$, n, m, p, $B^1$, W and Y are as herein-defined can be prepared by sulfonation of a hydroxymethylheterocyclic derivatives of formula (Vc):

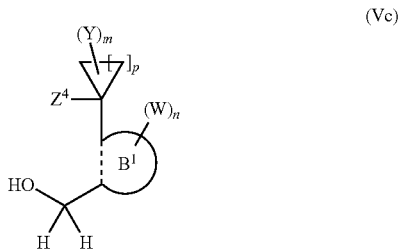

(Vc)

wherein $Z^4$, n, m, p, $B^1$, W and Y are as herein-defined, with a sulfonyl chloride in presence of a base (WO-2014/9495, step 3, page 61).

Carboxylic acid derivatives of formula (III) are known or can be prepared by known processes.

In case $U^1$ represents a hydroxy group, process P1 according to the present invention is conducted in the presence of condensing agent. Suitable condensing agent may be selected in the non limited list consisting of acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]-triazin-2-yl)-4-methylmorpholinium chloride hydrate, bromo-tripyrrolidinophosphoniumhexafluorophosphate or propanephosphonic anhydride (T3P).

Process P1 according to the present invention may be conducted in the presence of a catalyst. Suitable catalyst may be selected in the list consisting of N,N-dimethylpyridin-4-amine, 1-hydroxy-benzotriazole or N,N-dimethylformamide.

In case $U^1$ represents a halogen atom, process P1 according to the present invention is conducted in the presence of an acid binder. Suitable acid binders for carrying out process P1 according to the invention are in each case all inorganic and organic bases that are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as caesium carbonate, sodium carbonate, potassium carbonate, potassium bicarbonate, sodium bicarbonate, alkali metal or alkaline earth metal acetates, such as sodium acetate, potassium acetate, calcium acetate and also tertiary amines, such as trimethylamine, triethylamine, diisopropylethylamine, tributylamine, N,N-dimethylaniline, pyridine, N-methylpiperidine, N,N-dimethylpyridin-4-amine, diazabicyclooctane (DABCO), diazabicyclo-nonene (DBN) or diazabicycloundecene (DBU).

It is also possible to work in the absence of an additional condensing agent or to employ an excess of the amine component, so that it simultaneously acts as acid binder agent.

Suitable solvents for carrying out process P1 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone, or hexamethylphosphoric triamide; alcohols such as methanol, ethanol, propanol, iso-propanol; esters, such as methyl acetate or ethyl acetate, sulfoxides, such as dimethyl sulfoxide, or sulfones, such as sulfolane.

When carrying out process P1 according to the invention, the amine derivative of formula (II) can be employed as its salt, such as chlorhydrate or any other convenient salt.

When carrying out process P1 according to the invention, 1 mole or an excess of the amine derivative of formula (II) and from 1 to 3 moles of the acid binder can be employed per mole of the reagent of formula (III).

It is also possible to employ the reaction components in other ratios. Work-up is carried out by known methods.

According to a further aspect according to the invention, there is provided a second process P2 for the preparation of a compound of formula (I) wherein T represents S, starting from a compound of formula (I) wherein T represents O and illustrated according to the following reaction scheme:

Process P2

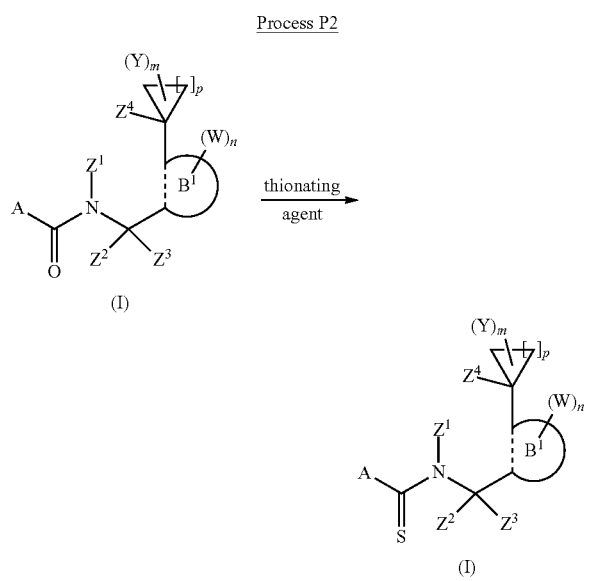

wherein A, $Z^1$, $Z^2$, $Z^3$, $Z^4$, n, m, p, $B^1$, W and Y are as herein-defined.

Process P2 according to the invention is performed in the presence of a thionating agent.

Starting amide derivatives of formula (I) wherein T represents O can be prepared according to process P1.

Suitable thionating agents for carrying out process P2 according to the invention can be sulfur (S), sulfhydric acid ($H_2S$), sodium sulfide ($Na_2S$), sodium hydrosulfide (NaHS), boron trisulfide ($B_2S_3$), bis(diethylaluminium) sulfide (($AlEt_2)_2S$), ammonium sulfide (($NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in Journal of the Chemical Society, Perkin 1 (2001), 358, in the optionally presence of a catalytic or stoichiometric or excess amount, quantity of a base such as an inorganic and organic base. Preference is given to using alkali metal carbonates, such as sodium carbonate, potassium carbonate, potassium bicarbonate, sodium bicarbonate; heterocyclic aromatic bases, such as pyridine, picoline, lutidine, collidine; and also tertiary amines, such as trimethylamine, triethylamine, tributylamine, N,N-dimethylaniline, N,N-dimethylpyridin-4-amine or N-methyl-piperidine.

Suitable solvents for carrying out process P2 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin, chlorobenzene, dichlorobenzene, dichloromethane, chloroform, carbon tetrachloride, dichlorethane or trichlorethane, ethers, such as diethyl ether, diisopropyl ether, methyl t-butyl ether, methyl t-amyl ether, dioxane, tetrahydrofuran, 1,2-dimethoxyethane or 1,2-diethoxyethane, nitriles, such as acetonitrile, propionitrile, n- or i-butyronitrile or benzonitrile, sulfurous solvents, such as sulfolane or carbon disulfide.

When carrying out process P2 according to the invention, 1 mole or an excess of the sulfur equivalent of the thionating agent and from 1 to 3 moles of the base can be employed per mole of the amide reactant (I).

It is also possible to employ the reaction components in other ratios. Work-up is carried out by known methods.

When carrying out processes P1 and P2 according to the invention, the reaction temperatures can be varied within a relatively wide range. In general, these processes are carried out at temperatures from 0° C. to 200° C., preferably from 10° C. to 150° C. A way to control the temperature for the processes according to the invention is to use microwave technology.

The present invention also relates to a process for the preparation of the compound of formula (IV) (Process P3):

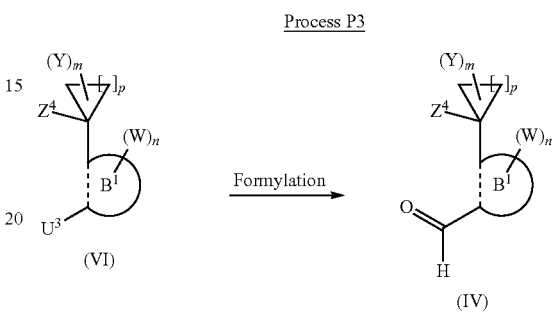

wherein $U^3$ is defined as bromo or iodo, and $Z^4$, n, m, p, $B^1$, W and Y are as herein-defined.

A compound of the general formula (IV) is obtained from a compound of the general formula (VI) by a formylation reaction, such as a reaction sequence of halogen-metal exchange with an organolithium or an organomagnesium reagent, followed by subsequent addition of an electrophile (e.g. N,N-dimethylformamide (DMF)) (*Journal of the American Chemical Society*, (2008), 130, 8481-8490). Alternatively, magnesium can be used to form a Grignard reagent from (VI), which can then be treated with an appropriate electrophile such as DMF to form a compound of the general formula (IV) (*Chemistry Letters*, (2007), 36, 72-73).

Process P3 is performed in the presence of a suitable organometallic compound or magnesium. Preferred organometallic compounds are organolithium compounds (such as butyllithium) or organomagnesium compounds (such us iso-propylmagnesium chloride or bromide).

Process P3 is preferably performed using one or more diluents. Useful solvents in the performance of process P3 are preferably aprotic solvents (such as dioxane, glyme, alkanes, cycloalkanes, diethyl ether or tetrahydrofuran). Particular preference is given to diethyl ether or tetrahydropyran.

In the performance of process P3, the reaction temperatures can be varied within a relatively wide range.

In the case of the halogen-metal exchange reactions, the temperatures employed are generally from −120° C. to 150° C., preferably temperatures from −120° C. to 60° C., most preferably −120° C. to 70° C. After the addition of an electrophile such as DMF, preference is given to working at −80° C. to 50° C.

To perform process P3, generally 1 to 2 mol, preferably 1 mol, of the organometallic compound and of the electrophile are used per mole of compound of the formula (VI).

The present invention also relates to processes for the preparation of the compound of formula (Va1) (Process P4):

Process P4

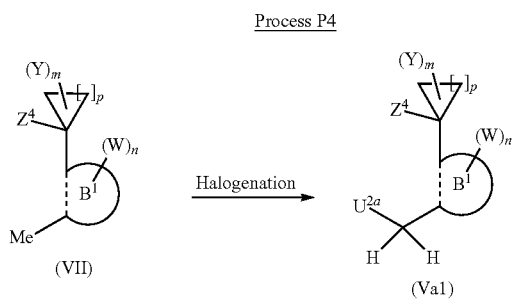

wherein $U^{2a}$ is a halogen, preferentially chloro, bromo and iodo, and $Z^4$, n, m, p, $B^1$, W and Y are as herein-defined.

A compound of the general formula (Va1) is obtained from a compound of the general formula (VII) by a radical halogenation of the methyl group (WO-2008/016239 and WO-2013/051632).

Process P4 is performed in the presence of a suitable halogenating reagent (such as n-chlorosuccinimide, n-bromosuccinimide, chlorine, bromine, iodine), and with a catalytic amount of a radical initiator such as 2,2'-Azobis(2-methylpropionitrile (AIBN).

Process P4 is preferably performed using one or more diluents. Useful solvents in the performance of process P4 are preferably inert solvents under radical halogenation conditions (such as carbon tetrachloride). Particular preference is given to carbon tetrachloride.

In the performance of process P4, the reaction temperatures can be varied within a relatively wide range. The temperatures employed are generally from –120° C. to 200° C., preferably temperatures from 80° C. to 150° C.

To perform process P4, 1 to 2 mol, preferably 1 mol, of a halogenating reagent are generally used per mole of compound of the formula (VII).

The present invention also relates to processes for the preparation of the compound of formula (VI) and (VII) wherein $Z^4$ is an electron withdrawing group (Process P5):

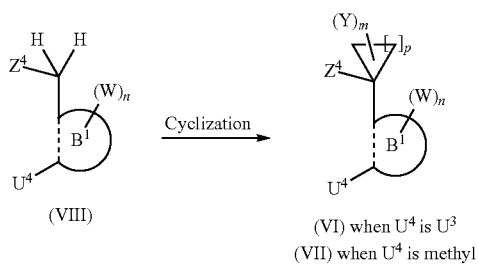

wherein $U^4$ is defined as methyl, chloro, bromo or iodo, and $Z^4$, n, m, p, $B^1$, W and Y are as herein-defined.

A compound of the general formula (VI) or (VII) is obtained from a compound of the general formula (VIII), wherein $Z^4$ is an electron withdrawing group (such as nitrile, carboxylic acid ester), by a cyclization reaction with a substituted or non-substituted alkyl chain which bears an appropriate leaving group, such as chloro, bromo, iodo, mesylate, tosylate or triflate, on each terminal carbon (such as 1,2-dibromoethane, 1,4-dibromobutane or 1,5-dibromopentane), in the presence of a suitable base, as mineral carbonates, such as potassium carbonate, sodium carbonate or caesium carbonate; metal hydroxides such as sodium hydroxide or potassium hydroxide; alkoxides, such as potassium tert-butoxide or sodium tert-butoxide; metal hydrides, such as sodium hydride; amides, such as lithium diisopropylamide (*Organic & Biomolecular Chemistry*, (2012), 10, 6404-6409 and WO-2011/041694). Process P5 can also be performed in the presence of an additive such as tetra-n-butylammonium bromide or N,N'-Dimethyl-N,N'-trimethyleneurea (DMPU).

To perform process P5, generally a stoichiometric or an excess amount of the substituted or non-substituted alkyl chain which bears an appropriate leaving group on each terminal carbon is used per mole of compound of the formula (VIII).

The solvents used may be all customary solvents which are inert under the reaction conditions, or the reaction can be performed in mixtures of two or more of these solvents.

In the performance of process P5, the reaction temperatures can be varied within a relatively wide range. In general, the temperatures employed are from –10° C. to 150° C., preferably temperatures from 0° C. to 100° C.

The present invention also relates to processes for the preparation of the compound of formula (VI) and (VII) wherein p is 1 (Process P6):

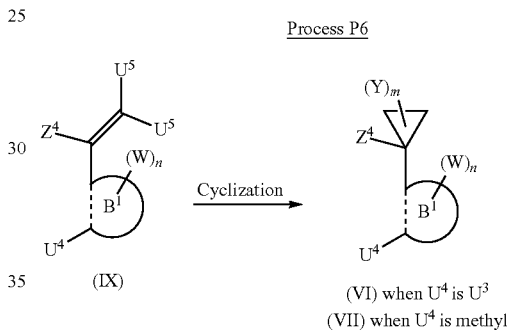

wherein $U^4$ is defined as methyl, chloro, bromo or iodo, $U^5$ is defined as hydrogen or Y, and $Z^4$, n, m, $B^1$, W and Y are as herein-defined.

A compound of the general formula (VI) or (VII) wherein p is 1, is obtained from a compound of the general formula (IX) by a cyclopropanation reaction such as the Simmons-Smith reaction (WO-2012/165648); cyclopropanation with a free carbene (*Chemical Reviews*, (2003), 103, 1099-1132); or cyclopropanation with a metal carbinoid (*Chemical Reviews*, (1987), 87, 411-432).

Alkenes derivatives (IX) are commercially available or can be prepared from commercially available precursors by methods described in the literature, from ketones by a Wittig or Horner-Wadsworth-Emmons olefination (*Chemical Reviews*, (1989), 89, 863-927); a Julia olefination (*Tetrahedron Letters*, (1973), 14, 4833-4836); a Peterson olefination (*Journal of Organic Chemistry*, (1968), 33, 780); or trapping of an electrophile by an enolate or an enol (WO-1991/11445).

The solvents used may be all customary solvents which are inert under the reaction conditions, or the reaction can be performed in mixtures of two or more of these solvents.

In the performance of process P6, the reaction temperatures can be varied within a relatively wide range.

In general, the temperatures employed are from –120° C. to 150° C., preferably temperatures from 80° C. to 100° C.

It is recognized that at any appropriate stage of synthesis, the substituent $Z^4$ can be converted from one substituent definition to another as specified above, in one or more steps, by synthetic methods commonly used by the person skilled in the art of chemical synthesis, for example, from a nitrile to a corresponding carboxylic acid by hydrolysis or to an aldehyde by reduction; from a carboxylic acid to a hydroxyalkyl by reduction; to a halogen by decarboxylative halogenation; from an aldehyde to a corresponding alkene or alkyne by a Wittig olefination or a Seyferth-Gilbert homologation.

Furthermore, it is also recognized that some reagents and reaction conditions described above for preparation of compounds of the formula (I) may not be compatible with particular functionalities present in the intermediate compounds. In these cases, the introduction of protection/deprotection sequences or of mutual conversions of functional groups into the synthesis helps to obtain the desired products. The use and selection of the protecting groups is obvious to the person skilled in the art of chemical synthesis (see, for example, "Protective Groups in Organic Synthesis"; Third Edition; 494-653, and literature cited therein). The person skilled in the art will recognize that, in some cases, after the introduction of a given reagent as shown in an individual scheme, it may be necessary to perform additional routine synthesis steps not described individually in order to complete the synthesis of compounds of the formula (I). The person skilled in the art will likewise recognize that it may be necessary to perform a combination of the steps illustrated in the above schemes in a sequence other than the implied sequence shown specifically, in order to prepare the compounds of the formula (I).

Processes P1 and P6 according to the invention are generally carried out under atmospheric pressure. It is also possible to operate under elevated or reduced pressure.

In general, the reaction mixture is concentrated under reduced pressure. The residue that remains can be freed by known methods, such as chromatography or crystallization, from any impurities that can still be present.

Work-up is carried out by customary methods. Generally, the reaction mixture is treated with water and the organic phase is separated off and, after drying, concentrated under reduced pressure. If appropriate, the remaining residue can, be freed by customary methods, such as chromatography, crystallization or distillation, from any impurities that may still be present.

The compound according to the present invention can be prepared according to the general processes of preparation described above. It will nevertheless be understood that, on the basis of his general knowledge and of available publications, the skilled worker will be able to adapt this method according to the specifics of each of the compounds, which it is desired to synthesize.

In a further aspect, the present invention also relates to a fungicide composition comprising an effective and non-phytotoxic amount of an active compound of formula (I).

The expression "effective and non-phytotoxic amount" means an amount of composition according to the invention that is sufficient to control or destroy the fungi present or liable to appear on the crops and that does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials that are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic, organic or inorganic compound with that the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulfonic acid salts, phenolsulfonic or naphthalenesulfonic acid salts, polycondensates of ethylene oxide with fatty alcohols or with fatty acids or with fatty amines, substituted phenols (in particular alkylphenols or arylphenols), salts of sulfosuccinic acid esters, taurine derivatives (in particular alkyl taurates), phosphoric esters of polyoxyethylated alcohols or phenols, fatty acid esters of polyols and derivatives of the above compounds containing sulfate, sulfonate and phosphate functions. The presence of at least one surfactant is generally essential when the active compound and/or the inert support are water-insoluble and when the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, that complies with the usual formulation techniques.

In general, the composition according to the invention can contain from 0.05 to 99% by weight of active compound, preferably 10 to 70% by weight.

Compositions according to the invention can be used in various forms and formulations such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions that are ready to be applied to the plant or seed to be treated by means of a suitable device, such as a spraying or dusting device, but also concentrated commercial compositions that must be diluted before application to the crop.

The formulations can be prepared in a manner known per se, for example by mixing the active ingredients with at least one customary extender, solvent or diluent, adjuvant, emulsifier, dispersant, and/or binder or fixative, wetting agent, water repellent, if appropriate desiccants and UV stabilizers and, if appropriate, dyes and pigments, antifoams, preservatives, inorganic and organic thickeners, adhesives, gibberellins and also further processing auxiliaries and also water. Depending on the formulation type to be prepared further processing steps are necessary, e.g. wet grinding, dry grinding and granulation.

The inventive active ingredients may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners biologicals, and/or semiochemicals.

The compounds of formula (I) and the fungicide composition according to the invention can be used to curatively or preventively control the phytopathogenic fungi of plants or crops, particularly rust diseases.

Thus, according to a further aspect of the invention, there is provided a method for curatively or preventively controlling the phytopathogenic fungi of plants or crops, particularly rust diseases, characterised in that a compound of formula (I) or a fungicide composition according to the invention is applied to the seed, the plant or to the fruit of the plant or to the soil wherein the plant is growing or wherein it is desired to grow.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

Among the plants that can be protected by the method according to the invention, mention may be made of major field crops like corn, soybean, cotton, *Brassica* oilseeds such as *Brassica napus* (e.g. canola), *Brassica rapa, B. juncea* (e.g. mustard) and *Brassica carinata*, rice, wheat, sugarbeet, sugarcane, oats, rye, barley, millet, triticale, flax, vine and various fruits and vegetables of various botanical taxa such as *Rosaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber—including pickling cucumber, squash, watermelon, gourds and melons), *Alliaceae* sp. (for instance onions and leek), *Cruciferae* sp. (for instance white cabbage, red cabbage, broccoli, cauliflower, brussel sprouts, pak choi, kohlrabi, radish, horseradish, cress, Chinese cabbage), *Leguminosae* sp. (for instance peanuts, peas and beans beans—such as climbing beans and broad beans), *Chenopodiaceae* sp. (for instance mangold, spinach beet, spinach, beetroots), *Malvaceae* (for instance okra), *Asparagaceae* (for instance asparagus); horticultural and forest crops; ornamental plants; as well as genetically modified homologues of these crops.

Wild plant species and plant cultivars, or those obtained by conventional biological breeding methods, such as crossing or protoplast fusion, and parts thereof, can be treated by the above disclosed methods. Transgenic plants and plant cultivars obtained by genetic engineering methods, if appropriate in combination with conventional methods (Genetically Modified Organisms), and parts thereof can be treated by the above disclosed methods. Preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The disclosed methods can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by down-regulating or silencing other gene(s) which are present in the plant (using for example, antisense technology, cosuppression technology, RNA interference-RNAi-technology or microRNA-miRNA-technology). A heterologous gene that is located in the genome is also called a transgene. A transgene that is defined by its particular location in the plant genome is called a transformation or transgenic event.

Plants and plant cultivars which can be treated by the above disclosed methods include all plants which have genetic material which impart particularly advantageous, useful traits to these plants (whether obtained by breeding and/or biotechnological means).

Plants and plant cultivars which can be treated by the above disclosed methods include plants and plant cultivars which are resistant against one or more biotic stresses, i.e. said plants show a better defense against animal and microbial pests, such as against nematodes, insects, mites, phytopathogenic fungi, bacteria, viruses and/or viroids.

Plants and plant cultivars which can be treated by the above disclosed methods include those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which can be treated by the above disclosed methods include those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants and plant cultivars which can be treated by the above disclosed methods include plants and plant cultivars which are hybrid plants that already express the characteristic of heterosis or hybrid vigor which results in generally higher yield, vigor, health and resistance towards biotic and abiotic stresses).

Plants and plant cultivars (obtained by plant biotechnology methods such as genetic engineering) which can be treated by the above disclosed methods include plants and plant cultivars which are herbicide-tolerant plants, i.e. plants made tolerant to one or more given herbicides. Such plants can be obtained either by genetic transformation, or by selection of plants containing a mutation imparting such herbicide tolerance.

Plants and plant cultivars (obtained by plant biotechnology methods such as genetic engineering) which can be treated by the above disclosed methods include plants and plant cultivars which are insect-resistant transgenic plants, i.e. plants made resistant to attack by certain target insects. Such plants can be obtained by genetic transformation, or by selection of plants containing a mutation imparting such insect for resistance.

Plants and plant cultivars (obtained by plant biotechnology methods such as genetic engineering) which can be treated by the above disclosed methods include plants and plant cultivars which are tolerant to abiotic stresses. Such plants can be obtained by genetic transformation, or by selection of plants containing a mutation imparting such stress resistance.

Plants and plant cultivars (obtained by plant biotechnology methods such as genetic engineering) which can be treated by the above disclosed methods include plants and plant cultivars which show altered quantity, quality and/or storage-stability of the harvested product and/or altered properties of specific ingredients of the harvested product.

Plants and plant cultivars (obtained by plant biotechnology methods such as genetic engineering) which can be treated by the above disclosed methods include plants and plant cultivars, such as cotton plants, with altered fiber characteristics. Such plants can be obtained by genetic transformation, or by selection of plants contain a mutation imparting such altered fiber characteristics.

Plants and plant cultivars (obtained by plant biotechnology methods such as genetic engineering) which can be treated by the above disclosed methods include plants and plant cultivars, such as oilseed rape or related *Brassica* plants, with altered oil profile characteristics. Such plants can be obtained by genetic transformation, or by selection of plants contain a mutation imparting such altered oil profile characteristics.

Plants and plant cultivars (obtained by plant biotechnology methods such as genetic engineering) which can be treated by the above disclosed methods include plants and plant cultivars, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants and plant cultivars (obtained by plant biotechnology methods such as genetic engineering) which can be treated by the above disclosed methods include plants and plant cultivars, such as Tobacco plants, with altered post-translational protein modification patterns.

Among the diseases of plants or crops that can be controlled by the method according to the invention, mention can be made of:

Powdery mildew diseases such as:
*Blumeria* diseases, caused for example by *Blumeria* graminis;
*Podosphaera* diseases, caused for example by *Podosphaera* leucotricha;
*Sphaerotheca* diseases, caused for example by *Sphaerotheca* fuliginea;
*Uncinula* diseases, caused for example by *Uncinula* necator;

Rust diseases such as:
*Gymnosporangium* diseases, caused for example by *Gymnosporangium* sabinae;
*Hemileia* diseases, caused for example by *Hemileia* vastatrix;
*Phakopsora* diseases, caused for example by *Phakopsora* pachyrhizi or *Phakopsora* meibomiae;
*Puccinia* diseases, caused for example by *Puccinia* recondite, *Puccinia graminis* or *Puccinia* striiformis;
*Uromyces* diseases, caused for example by *Uromyces* appendiculatus;

Oomycete diseases such as:
*Albugo* diseases caused for example by *Albugo* candida;
*Bremia* diseases, caused for example by *Bremia* lactucae;
*Peronospora* diseases, caused for example by *Peronospora pisi* or *P. brassicae;*
*Phytophthora* diseases, caused for example by *Phytophthora* infestans;
*Plasmopara* diseases, caused for example by *Plasmopara* viticola;
*Pseudoperonospora* diseases, caused for example by *Pseudoperonospora humuli* or *Pseudoperonospora* cubensis;
*Pythium* diseases, caused for example by *Pythium* ultimum;

Leafspot, leaf blotch and leaf blight diseases such as:
*Alternaria* diseases, caused for example by *Alternaria* solani;
*Cercospora* diseases, caused for example by *Cercospora* beticola;
*Cladiosporum* diseases, caused for example by *Cladiosporium cucumerinum;*

*Cochliobolus* diseases, caused for example by *Cochliobolus sativus* (Conidiaform: Drechslera, Syn: Helminthosporium) or *Cochliobolus miyabeanus*;

*Colletotrichum* diseases, caused for example by *Colletotrichum lindemuthanium*;

*Cycloconium* diseases, caused for example by *Cycloconium oleaginum*;

*Diaporthe* diseases, caused for example by *Diaporthe citri*;

*Elsinoe* diseases, caused for example by *Elsinoe* fawcettii;

*Gloeosporium* diseases, caused for example by *Gloeosporium laeticolor*;

*Glomerella* diseases, caused for example by *Glomerella cingulata*;

*Guignardia* diseases, caused for example by *Guignardia bidwelli*;

*Leptosphaeria* diseases, caused for example by *Leptosphaeria maculans*; *Leptosphaeria nodorum*;

*Magnaporthe* diseases, caused for example by *Magnaporthe grisea*;

*Mycosphaerella* diseases, caused for example by *Mycosphaerella graminicola*; *Mycosphaerella arachidicola*; *Mycosphaerella fijiensis*;

*Phaeosphaeria* diseases, caused for example by *Phaeosphaeria nodorum*;

*Pyrenophora* diseases, caused for example by *Pyrenophora teres*, or *Pyrenophora tritici repentis*;

*Ramularia* diseases, caused for example by *Ramularia collocygni*, or *Ramularia areola*;

*Rhynchosporium* diseases, caused for example by *Rhynchosporium secalis*;

*Septoria* diseases, caused for example by *Septoria apii* or *Septoria lycopercisi*;

*Typhula* diseases, caused for example by *Typhula incamata*;

*Venturia* diseases, caused for example by *Venturia inaequalis*;

Root, Sheath and stem diseases such as:

*Corticium* diseases, caused for example by *Corticium graminearum*;

*Fusarium* diseases, caused for example by *Fusarium oxysporum*;

*Gaeumannomyces* diseases, caused for example by *Gaeumannomyces graminis*;

*Rhizoctonia* diseases, caused for example by *Rhizoctonia solani*;

*Sarocladium* diseases caused for example by *Sarocladium oryzae*;

*Sclerotium* diseases caused for example by *Sclerotium oryzae*;

*Tapesia* diseases, caused for example by *Tapesia acuformis*;

*Thielaviopsis* diseases, caused for example by *Thielaviopsis basicola*;

Ear and panicle diseases such as:

*Alternaria* diseases, caused for example by *Alternaria* spp.;

*Aspergillus* diseases, caused for example by *Aspergillus flavus*;

*Cladosporium* diseases, caused for example by *Cladosporium* spp.;

*Claviceps* diseases, caused for example by *Claviceps purpurea*;

*Fusarium* diseases, caused for example by *Fusarium culmorum*;

*Gibberella* diseases, caused for example by *Gibberella zeae*;

*Monographella* diseases, caused for example by *Monographella nivalis*;

Smut and bunt diseases such as:

*Sphacelotheca* diseases, caused for example by *Sphacelotheca reiliana*;

*Tilletia* diseases, caused for example by *Tilletia caries*;

*Urocystis* diseases, caused for example by *Urocystis occulta*;

*Ustilago* diseases, caused for example by *Ustilago nuda*;

Fruit rot and mould diseases such as:

*Aspergillus* diseases, caused for example by *Aspergillus flavus*;

*Botrytis* diseases, caused for example by *Botrytis cinerea*;

*Penicillium* diseases, caused for example by *Penicillium expansum*;

*Rhizopus* diseases caused by example by *Rhizopus stolonifer*

*Sclerotinia* diseases, caused for example by *Sclerotinia sclerotiorum*;

*Verticilium* diseases, caused for example by *Verticilium alboatrum*;

Seed and soilborne decay, mould, wilt, rot and damping-off diseases:

*Alternaria* diseases, caused for example by *Alternaria brassicicola*;

*Aphanomyces* diseases, caused for example by *Aphanomyces euteiches*;

*Ascochyta* diseases, caused for example by *Ascochyta lentis*;

*Aspergillus* diseases, caused for example by *Aspergillus flavus*;

*Cladosporium* diseases, caused for example by *Cladosporium herbarum*;

*Cochliobolus* diseases, caused for example by *Cochliobolus sativus*;

(Conidiaform: *Drechslera*, *Bipolaris* Syn: *Helminthosporium*);

*Colletotrichum* diseases, caused for example by *Colletotrichum coccodes*;

*Fusarium* diseases, caused for example by *Fusarium culmorum*;

*Gibberella* diseases, caused for example by *Gibberella zeae*;

*Macrophomina* diseases, caused for example by *Macrophomina phaseolina*;

*Monographella* diseases, caused for example by *Monographella nivalis*;

*Penicillium* diseases, caused for example by *Penicillium expansum*;

*Phoma* diseases, caused for example by *Phoma lingam*;

*Phomopsis* diseases, caused for example by *Phomopsis sojae*;

*Phytophthora* diseases, caused for example by *Phytophthora cactorum*;

*Pyrenophora* diseases, caused for example by *Pyrenophora graminea*;

*Pyricularia* diseases, caused for example by *Pyricularia oryzae*;

*Pythium* diseases, caused for example by *Pythium ultimum*;

*Rhizoctonia* diseases, caused for example by *Rhizoctonia solani*;

*Rhizopus* diseases, caused for example by *Rhizopus oryzae*;

*Sclerotium* diseases, caused for example by *Sclerotium rolfsii*;

*Septoria* diseases, caused for example by *Septoria* nodorum;
*Typhula* diseases, caused for example by *Typhula* incarnate;
*Verticillium* diseases, caused for example by *Verticillium* dahliae;
Canker, broom and dieback diseases such as:
*Nectria* diseases, caused for example by *Nectria* galligena;
Blight diseases such as:
*Monilinia* diseases, caused for example by *Monilinia* lexa;
Leaf blister or leaf curl diseases such as:
*Exobasidium* diseases caused for example by *Exobasidium* vexans;
*Taphrina* diseases, caused for example by *Taphrina* deformans;
Decline diseases of wooden plants such as:
Esca diseases, caused for example by *Phaemoniella clamydospora*;
*Eutypa* dyeback, caused for example by *Eutypa* late;
*Ganoderma* diseases caused for example by *Ganoderma* boninense;
*Rigidoporus* diseases caused for example by *Rigidoporus* lignosus;
Diseases of Flowers and Seeds such as:
*Botrytis* diseases caused for example by *Botrytis* cinerea;
Diseases of Tubers such as:
*Rhizoctonia* diseases caused for example by *Rhizoctonia* solani;
*Helminthosporium* diseases caused for example by *Helminthosporium* solani;
Club root diseases such as:
*Plasmodiophora* diseases, cause for example by *Plamodiophora brassicae*;
Diseases caused by *Bacterial Organisms such as:*
*Xanthomonas* species for example *Xanthomonas campestris* pv. oryzae;
*Pseudomonas* species for example *Pseudomonas syringae* pv. lachrymans;
*Erwinia* species for example *Erwinia* amylovora.

The composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The compounds or mixtures according to the invention can also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus* fumigatus.

The present invention further relates to the use of compounds of the formula (I) as herein defined for the control of phytopathogenic fungi.

The present invention further relates to the use of compounds of the formula (I) as herein defined for the treatment of transgenic plants.

The present invention further relates to the use of compounds of the formula (I) as herein defined for the treatment of seed and of seed of transgenic plants.

The present invention further relates to a process for producing compositions for controlling phytopathogenic harmful fungi, characterized in that derivatives of the formula (I) as herein defined are mixed with extenders and/or surfactants. The various aspects of the invention will now be illustrated with reference to the following table of compound examples and the following preparation or efficacy examples.

Table 1 illustrates in a non-limiting manner examples of compounds of formula (I) according to the invention:

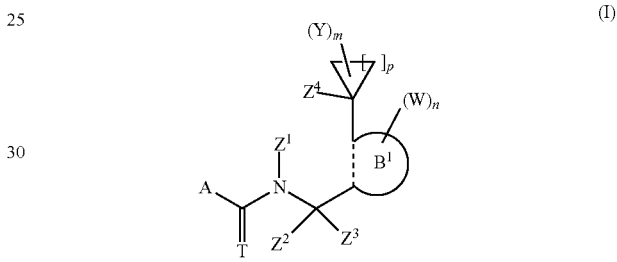

wherein A can be selected in the list consisting of the following groups: A-G1 and A-G2:

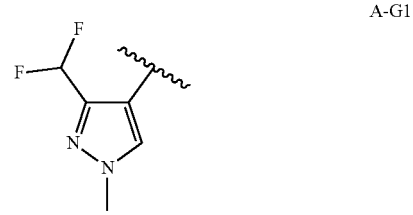

A-G1

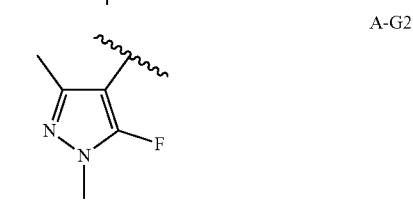

A-G2

In table 1, unless otherwise specified, M+H (Apcl+) means the molecular ion peak plus 1 a.m.u. (atomic mass unit) as observed in mass spectroscopy via positive atmospheric pressure chemical ionisation.

In table 1, the logP values were determined in accordance with EEC Directive 79/831 Annex V.A8 by HPLC (High Performance Liquid Chromatography) on a reversed-phase column (C 18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known logP values (determination of the logP values by the retention times using linear interpolation between two successive alkanones). lambda-max-values were determined using UV-spectra from 200 nm to 400 nm and the peak values of the chromatographic signals.

In table 1, "position" denotes the point of attachment of the 1-substitutedcycloalkyl residue to the $B^1$ heterocyclyl ring based on the IUPAC numbering of heterocyclic rings.

stereoisomers of the target compounds, which are also object of the invention, and/or peaks of impurities. To show compound signals in the delta-range of solvents and/or water the usual peaks of solvents, for example peaks of DMSO in d6-DMSO and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%). Such stereoisomers and/or impurities

TABLE 1

| Example | A | T | $Z^1$ | $Z^2$ | $Z^3$ | $B^1$ | $(W)_n$ | Position | * | M + H | logP |
|---|---|---|---|---|---|---|---|---|---|---|---|
| I.01 | A-G1 | O | cyclopropyl | H | H | pyridin-3-yl | 5-Br | 2- | 1-methylcyclopropyl | 439 | 2.51 |
| I.02 | A-G1 | O | cyclopropyl | H | H | 2-thienyl |  | 3- | 1-methylcyclopropyl | 388[1] | 3.33 |
| I.03 | A-G2 | O | cyclopropyl | H | H | 2-thienyl | 5-Me | 3- | 1-methylcyclopropyl | 362 | 3.64 |
| I.04 | A-G1 | O | cyclopropyl | H | H | 2-thienyl |  | 3- | 1-chlorocyclopropyl | 386 | 3.04 |
| I.05 | A-G1 | O | cyclopropyl | H | H | 2-thienyl | 5-Me | 3- | 1-chlorocyclopropyl | 400 | 3.39 |
| I.06 | A-G1 | S | cyclopropyl | H | H | 2-thienyl |  | 3- | 1-methylcyclopropyl | 382 | 3.88 |
| I.07 | A-G1 | S | cyclopropyl | H | H | 2-thienyl |  | 3- | 1-chlorocyclopropyl | 402 | 3.76 |
| I.08 | A-G1 | S | cyclopropyl | H | H | 2-thienyl | 5-Me | 3- | 1-chlorocyclopropyl | 416 | 4.14 |
| I.09 | A-G1 | O | cyclopropyl | H | H | pyridin-3-yl | 5-phenyl | 2- | 1-methylcyclopropyl | 437 | 1.97 |
| I.10 | A-G1 | O | cyclopropyl | H | H | pyridin-3-yl | 5-(cyclopent- | 2- | 1-methylcyclopropyl | 427 | 1.94 |

Note:
[1] M + Na ion

Note:
Me: methyl

Table 2 provides the NMR data ($^1$H) of a selected number of compounds from table 1.

The $^1$H-NMR data of selected examples are stated in the form of $^1$H-NMR peak lists. For each signal peak, the δ value in ppm and the signal intensity in brackets are listed.

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

The $^1$H-NMR peak lists are similar to classical $^1$H-NMR prints and contain therefore usually all peaks, which are listed at classical NMR-interpretation. Additionally they can show like classical $^1$H-NMR prints signals of solvents, can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values), can isolate the peaks of the target compounds as needed optionally using additional intensity filters. This isolation would be similar to relevant peak picking at classical $^1$H-NMR interpretation.

Further details of NMR-data description with peak lists can be found in the publication "Citation of NMR Peaklist Data within Patent Applications" of the Research Disclosure Database Number 564025.

TABLE 2

NMR peak lists

Example I.01: $^1$H-NMR (400 MHz, $d_6$-DMSO):
8.488 (4.3); 8.483 (5.0); 7.960 (1.6); 7.540 (3.6); 7.535 (3.5); 7.296 (1.6); 7.160 (3.7); 7.024 (1.8); 4.886 (8.0); 3.959 (15.1); 3.322 (2.5); 3.091 (0.9); 2.898 (12.6); 2.739 (10.0); 2.738 (10.3); 2.531 (0.4); 2.518 (9.3); 2.513 (19.2); 2.509 (26.1); 2.504 (18.6); 2.500 (8.8); 1.348 (16.0); 0.950 (1.2); 0.938 (4.0); 0.934 (4.3); 0.924 (1.7); 0.823 (0.7); 0.805 (4.7); 0.790 (7.1); 0.778 (1.9); 0.602 (0.9); 0.590 (2.7); 0.585 (2.9); 0.581 (2.7); 0.576 (2.5); 0.563 (0.7)

Example I.02: 1H-NMR (400 MHz, $d_6$-DMSO):
8.365 (2.3); 7.296 (1.5); 7.259 (5.2); 7.246 (5.5); 7.161 (3.3); 7.025 (1.6); 6.908 (5.4); 6.895 (5.0); 5.758 (0.4); 4.911 (10.4); 3.926 (16.0); 3.368 (0.4); 3.318 (126.7); 3.268 (1.0); 2.954 (0.8); 2.531 (0.5); 2.526 (0.9); 2.518 (12.2); 2.513 (25.3); 2.509 (34.6); 2.504 (24.5); 2.500 (11.4); 2.459 (0.3); 1.275 (15.2); 0.843 (0.6); 0.829 (2.2); 0.825 (2.7); 0.812 (2.8); 0.808 (2.4); 0.795 (0.8); 0.754 (1.1); 0.738 (4.1); 0.730 (2.0); 0.720 (0.9); 0.695 (0.8); 0.686 (2.4); 0.678 (4.7); 0.674 (3.7); 0.662 (1.3); 0.650 (1.0); 0.639 (2.7); 0.632 (3.0); 0.623 (2.5); 0.611 (0.7)

Example I.03: $^1$H-NMR (300 MHz, $CDCl_3$):
7.269 (2.0); 6.552 (3.0); 6.549 (3.2); 4.919 (5.2); 3.682 (10.1); 3.680 (10.6); 2.880 (0.7); 2.377 (11.2); 2.328 (16.0); 2.303 (0.4); 1.731 (0.6); 1.281 (12.2); 0.767 (1.0); 0.748 (4.2); 0.737 (3.2); 0.718 (1.8); 0.696 (1.0); 0.672 (0.5); 0.646 (2.0); 0.634 (4.5); 0.627 (4.5); 0.613 (3.1); 0.585 (0.5); 0.072 (0.9); 0.000 (2.0)

TABLE 2-continued

NMR peak lists

Example I.04: $^1$H-NMR (400 MHz, $d_6$-DMSO):
8.379 (2.9); 7.367 (3.7); 7.354 (4.0); 7.305 (1.4); 7.169 (3.0); 7.085 (4.0); 7.072 (3.7); 7.034 (1.5); 5.759 (1.9); 4.996 (10.1); 3.929 (16.0); 3.315 (44.5); 2.989 (1.1); 2.508 (38.7); 1.450 (1.2); 1.431 (4.5); 1.418 (2.1); 1.376 (0.7); 1.335 (2.0); 1.321 (4.4); 1.302 (1.2); 0.861 (0.7); 0.843 (3.0); 0.830 (3.1); 0.813 (0.9); 0.672 (1.0); 0.661 (3.0); 0.654 (3.4); 0.646 (2.7); 0.633 (0.8)

Example I.05: $^1$H-NMR (400 MHz, $d_6$-DMSO):
8.369 (2.9); 7.302 (1.3); 7.166 (2.9); 7.030 (1.4); 6.765 (4.5); 5.759 (2.8); 4.918 (8.7); 3.927 (16.0); 3.314 (62.1); 2.974 (1.1); 2.678 (0.3); 2.509 (60.4); 2.346 (14.6); 1.415 (1.2); 1.396 (4.4); 1.383 (2.0); 1.341 (0.6); 1.299 (2.0); 1.285 (4.3); 1.266 (1.2); 0.858 (0.7); 0.840 (3.0); 0.827 (3.0); 0.811 (0.9); 0.665 (1.0); 0.654 (3.0); 0.647 (3.3); 0.639 (2.7); 0.626 (0.8)

Example I.09: $^1$H NMR (300 MHz, $CDCl_3$):
8.705 (5.4); 8.697 (5.5); 8.257 (2.3); 7.756 (1.4); 7.629 (4.5); 7.622 (4.5); 7.579 (3.4); 7.574 (5.0); 7.551 (8.3); 7.547 (7.8); 7.514 (2.8); 7.510 (4.0); 7.503 (1.7); 7.486 (7.8); 7.461 (4.0); 7.441 (2.0); 7.436 (3.4); 7.431 (2.1); 7.421 (1.2); 7.412 (3.4); 7.402 (0.7); 7.388 (1.0); 7.315 (1.4); 7.298 (24.7); 7.132 (2.3); 6.949 (1.2); 5.335 (8.2); 5.115 (8.2); 4.017 (16.0); 2.957 (0.5); 2.943 (1.3); 2.934 (1.5); 2.921 (2.2); 2.908 (1.5); 2.899 (1.3); 2.886 (0.6); 2.229 (0.8); 2.223 (0.8); 2.190 (0.7); 2.042 (0.4); 1.498 (17.3); 1.290 (1.1); 1.088 (5.8); 0.985 (0.4); 0.935 (3.1); 0.921 (7.8); 0.916 (7.7); 0.900 (2.2); 0.836 (0.8); 0.817 (3.4); 0.794 (3.9); 0.777 (2.2); 0.749 (2.0); 0.734 (5.0); 0.694 (0.8); 0.118 (1.3); 0.106 (30.7); 0.093 (1.3); 0.081 (0.4); 0.046 (0.7); 0.035 (18.8); 0.024 (0.8)

Example I.10: $^1$H NMR (300 MHz, $CDCl_3$):
8.519 (6.4); 8.513 (6.4); 8.222 (0.3); 8.012 (0.4); 7.754 (1.2); 7.442 (0.8); 7.427 (5.4); 7.422 (5.4); 7.318 (1.4); 7.302 (10.7); 7.197 (0.4); 7.178 (0.6); 7.170 (0.4); 7.148 (0.9); 7.135 (2.7); 6.953 (1.4); 6.218 (4.5); 5.428 (0.8); 5.332 (14.2); 5.038 (8.6); 4.027 (16.0); 2.925 (0.8); 2.912 (1.6); 2.902 (2.0); 2.889 (2.8); 2.876 (1.9); 2.867 (1.6); 2.853 (0.8); 2.704 (2.2); 2.697 (2.6); 2.688 (2.5); 2.673 (4.5); 2.654 (3.0); 2.647 (2.8); 2.573 (2.3); 2.565 (2.5); 2.549 (4.3); 2.542 (4.2); 2.524 (3.1); 2.516 (2.7); 2.204 (0.3); 2.083 (1.8); 2.057 (4.8); 2.033 (6.2); 2.008 (4.1); 1.983 (1.5); 1.954 (0.4); 1.922 (0.4); 1.508 (0.5); 1.486 (0.8); 1.478 (0.8); 1.440 (19.5); 1.352 (0.4); 1.312 (0.9); 1.286 (3.1); 1.084 (0.5); 1.022 (6.8); 0.952 (0.7); 0.927 (1.2); 0.910 (0.7); 0.877 (4.5); 0.863 (10.1); 0.858 (9.2); 0.842 (2.9); 0.787 (4.4); 0.766 (4.4); 0.749 (2.4); 0.696 (5.8); 0.682 (4.9); 0.103 (2.5); 0.041 (0.3); 0.030 (8.3); 0.019 (0.4)

The following examples illustrate in a non-limiting manner the preparation and efficacy of the compounds of formula (I) according to the invention.

PREPARATION EXAMPLE 1

Preparation of N-{[3-(1-chlorocyclopropyl)-5-methyl-2-thienyl]methyl}-N-cyclopropyl-3-(difluoromethyl)-1-methyl-1H-pyrazole-4-carboxamide (Compound I.05)

Step 1: N-{[3-(1-chlorocyclopropyl)-5-methyl-2-thienyl]methyl}cyclopropanamine (Compound IIa.03)

To a cooled mixture of 960 mg (4.78 mmol) of 3-(1-chlorocyclopropyl)-5-methylthiophene-2-carbaldehyde (compound V.02) and 546 mg (9.57 mmol) of cyclopropylamine in 10 mL of methanol are added 3 g of 3 Å molecular sieves followed by a slow addition of 718 mg (12 mmol) of acetic acid. The reaction mixture is stirred for 90 min at reflux. The reaction mixture is then cooled to room temperature and 4.06 g (18.11 mmol) of sodium cyanoborohydride are slowly added. The reaction mixture is further stirred for 5 h at reflux. The cooled reaction mixture is then filtered over a cake of diatomaceous earth and the cake washed by methanol. Concentration leaves a residue that is dissolved by ethyl acetate, washed by a 1N aqueous solution of sodium hydroxide followed by a saturated aqueous solution of NaCl. The organic phase is dried, concentrated and purified by column chromatography on silica gel (gradient n-heptane/ethyl acetate) to provide 400 mg (33% yield) of N-{[3-(1-chlorocyclopropyl)-5-methyl-2-thienyl]-methyl}cyclopropanamine. LogP=1.20. Mass (M+H)=242.

Step 2: Preparation of N-{[3-(1-chlorocyclopropyl)-5-methyl-2-thienyl]methyl}-N-cyclopropyl-3-(difluoromethyl)-1-methyl-1H-pyrazole-4-carboxamide In a dried Radleys™ vial, a solution of 80 mg (0.41 mmol) of 3-(difluoromethyl)-1-methyl-1H-pyrazole-4-carbonyl chloride in 2 mL of dry tetrahydrofuran is added to a mixture of 95 mg (0.39 mmol) of N-{[3-(1-chlorocyclopropyl)-5-methyl-2-thienyl]methyl}cyclopropanamine and 44 mg (0.43 mmol) of triethylamine in 3 mL of dry tetrahydrofuran. The reaction mixture is stirred at room temperature for 1 h. The reaction mixture is then filtered over a basic alumina cartridge and the cartridge washed by tetrahydrofuran. Concentration and purification of the residue by preparative HPLC (gradient acetonitrile/water+0.1% $HCO_2H$) provides 101 mg (61% yield) of N-{[3-(1-chlorocyclopropyl)-5-methyl-2-thienyl]-methyl}-N-cyclopropyl-3-(difluoromethyl)-1-methyl-1H-pyrazole-4-carboxamide. LogP=3.39. Mass (M+H)=400.

General Preparation Example 2: Thionation of Amide of Formula (I) on Chemspeed™ Apparatus In a 13 mL Chemspeed™ vial is weighted 0.27 mmol of phosphorous pentasulfide ($P_2S_5$). 3 mL of a 0.18 M solution of the amide (I) (0.54 mmol) in dioxane is added and the mixture is heated at reflux for two hours. The temperature is then cooled to 80° C. and 2.5 mL of water are added. The mixture is heated at 80° C. for one more hour. 2 mL of water are then added and the reaction mixture is extracted twice by 4 mL of dichloromethane. The organic phase is deposited on a basic alumina cartridge (2 g) and eluted twice by 8 mL of dichloromethane. The solvents are removed and the crude thioamide derivative is analyzed by LCMS and NMR. Insufficiently pure compounds are further purified by preparative LC.

Example A: In Vivo Preventive Test on *Puccinia Recondita* (Brown Rust on Wheat)

Solvent: 5% by volume of Dimethyl sulfoxide
10% by volume of Acetone
Emulsifier: 1 µL of Tween® 80 per mg of active ingredient The active ingredients are made soluble and homogenized in a mixture of Dimethyl sulfoxide/Acetone/Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Puccinia recondita* spores. The contaminated wheat plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy between 70% and 79% at a concentration of 100 ppm of active ingredient: I.06

In this test the following compounds according to the invention showed efficacy between 90% and 100% at a concentration of 100 ppm of active ingredient: I.01; I.02; I.03

Under the same conditions, excellent (at least 90%) protection was observed at a dose of 100 ppm of active ingredient with compound of example I.01, whereas no protection was observed with compound CMP1 (isopropyl analogue) disclosed in patent application WO2008/037789 as in table A2:

TABLE A2

| Example | dose (ppm) | Efficacy |
|---|---|---|
| I.01 from this patent | 100 | 98 |
| CMP1 from WO2008/037789 | 100 | 0 |

Example CMP1 disclosed in international patent WO2008/037789 corresponds to N-[(5-chloro-2-isopropylpyridin-3-yl)methyl]-N-cyclopropyl-3-(difluoromethyl)-1-methyl-1H-pyrazole-4-carboxamide.

These results showed that the compounds according to the invention have a much better biological activity than the structurally closest compounds disclosed in WO2008/037789.

Example B: In Vivo Preventive Test on *Uromyces Appendiculatus* (Bean Rust)

Solvent: 5% by volume of Dimethyl sulfoxide
10% by volume of Acetone
Emulsifier: 1 µL of Tween® 80 per mg of active ingredient The active ingredients are made soluble and homogenized in a mixture of Dimethyl sulfoxide/Acetone/Tween® 80 and then diluted in water to the desired concentration.

The young plants of bean are treated by spraying the active ingredient prepared as described above.

Control plants are treated only with an aqueous solution of Acetone/Dimethyl sulfoxide/Tween® 80.

After 24 hours, the plants are contaminated by spraying the leaves with an aqueous suspension of *Uromyces appendiculatus* spores. The contaminated bean plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy between 90% and 100% at a concentration of 100 ppm of active ingredient: I.01; I.03

Under the same conditions, excellent (at least 90%) protection was observed at a dose of 100 ppm of active ingredient with compound of example I.01, whereas no protection was observed with compound CMP1 (isopropyl analogue) disclosed in patent application WO2008/037789 as in table B2:

TABLE B2

| Example | dose (ppm) | Efficacy |
|---|---|---|
| I.01 from this patent | 100 | 91 |
| CMP1 from WO2008/037789 | 100 | 0 |

Example CMP1 disclosed in international patent WO2008/037789 corresponds to N-[(5-chloro-2-isopropylpyridin-3-yl)methyl]-N-cyclopropyl-3-(difluoromethyl)-1-methyl-1H-pyrazole-4-carboxamide.

These results showed that the compounds according to the invention have a much better biological activity than the structurally closest compounds disclosed in WO2008/037789.

The invention claimed is:

1. A compound of formula (I)

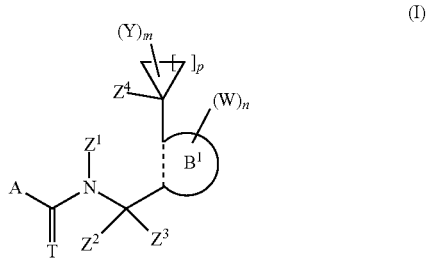

wherein:
A is a carbo-linked, unsaturated or partially saturated, 5-membered heterocyclyl group that can be substituted by up to four groups R that can be the same or different, provided that A is not a 3-(dihalogenomethyl)-5-halogeno-1-methyl-1H-pyrazol-4-yl group wherein the halogeno atoms are independently a fluoro or chloro atom;
T is O or S;
n is 0, 1, 2, 3 or 4;
m is 0, 1, 2, 3, 4, 5 or 6;
p is 1, 2, 3, 4 or 5;
$Z^1$ is a non-substituted $C_3$-$C_7$-cycloalkyl or a $C_3$-$C_7$-cycloalkyl substituted by up to 10 atoms or groups that can be the same or different and that can be selected in the list consisting of halogen atoms, cyano, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl and di-$C_1$-$C_8$-alkylaminocarbonyl;
$Z^2$ and $Z^3$ are independently a hydrogen atom; substituted or non-substituted $C_1$-$C_8$-alkyl; substituted or non-substituted $C_2$-$C_8$-alkenyl; substituted or non-substituted $C_2$-$C_8$-alkynyl; cyano; isonitrile; nitro; a halogen atom; substituted or non-substituted $C_1$-$C_8$-alkoxy; substituted or non-substituted $C_2$-$C_8$-alkenyloxy; substituted or non-substituted $C_2$-$C_8$-alkynyloxy; substituted or non-substituted $C_3$-$C_7$-cycloalkyl; substituted or non-substituted $C_1$-$C_8$-alkylsulfanyl; substituted or non-substituted $C_1$-$C_8$-alkylsulfonyl; substituted or non-substituted $C_1$-$C_8$-alkylsulfinyl; amino; substituted or non-substituted $C_1$-$C_8$-alkylamino; substituted or non-substituted di-$C_1$-$C_8$-alkylamino; substituted or non-substituted $C_1$-$C_8$-alkoxycarbonyl; substituted or non-substituted $C_1$-$C_8$-alkylcarbamoyl; substituted or non-substituted di-$C_1$-$C_8$-alkylcarbamoyl; or substituted or non-substituted N—$C_1$-$C_8$-alkyl-$C_1$-$C_8$-alkoxy-carbamoyl; or $Z^2$ and $Z^3$ together with the carbon atom to which they are linked can form a substituted or non-substituted $C_3$-$C_7$-cycloalkyl;

$Z^4$ is a halogen atom; hydroxy; cyano; substituted or non-substituted $C_1$-$C_8$-alkyl; $C_1$-$C_8$-halogenoalkyl having 1 to 5 halogen atoms; substituted or non-substituted $C_2$-$C_8$-alkenyl; $C_2$-$C_8$-halogenoalkenyl having 1 to 5 halogen atoms; substituted or non-substituted $C_2$-$C_8$-alkynyl; $C_2$-$C_8$-halogenoalkynyl having 1 to 5 halogen atoms; substituted or non-substituted $C_1$-$C_8$-alkoxy; $C_1$-$C_8$-halogenoalkoxy having 1 to 5 halogen atoms; substituted or non-substituted $C_1$-$C_8$-alkylsulfanyl; formyl; substituted or non-substituted $C_1$-$C_8$-alkylcarbonyl; carboxy; or substituted or non-substituted $C_1$-$C_8$-alkoxycarbonyl;

$B^1$ is a carbo-linked unsaturated, monocyclic or fused bicyclic 5-, 6-, 8-, 9-, 10-membered heterocyclyl ring comprising from 1 up to 4 heteroatoms selected in the list consisting of N, O, S; wherein the dotted line between the two adjacent carbons is a single bond, a double bond or an aromatic bond, with the proviso that $B^1$ is not a 1,3-benzodioxolyl group;

each W is independently a halogen atom; nitro; cyano; isonitrile; hydroxy; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-halogenoalkyl having 1 to 9 halogen atoms; substituted or non-substituted $C_2$-$C_8$-alkenyl; $C_2$-$C_8$-halogenoalkenyl having 1 to 9 halogen atoms; substituted or non-substituted $C_2$-$C_8$-alkynyl; $C_2$-$C_8$-halogenoalkynyl having 1 to 9 halogen atoms; substituted or non-substituted $C_1$-$C_8$-alkoxy; $C_1$-$C_8$-halogenoalkoxy having 1 to 9 halogen atoms; substituted or non-substituted $C_1$-$C_8$-alkylsulfanyl; $C_1$-$C_8$-halogenoalkylsulfanyl having 1 to 9 halogen atoms; substituted or non-substituted $C_1$-$C_8$-alkylsulfinyl; $C_1$-$C_8$-halogenoalkylsulfinyl having 1 to 9 halogen atoms; substituted or non-substituted $C_1$-$C_8$-alkylsulfonyl; $C_1$-$C_8$-halogenoalkylsulfonyl having 1 to 9 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-halogenoalkenyloxy having 1 to 9 halogen atoms; substituted or non-substituted $C_3$-$C_8$-alkynyloxy; $C_2$-$C_8$-halogenoalkynyloxy having 1 to 9 halogen atoms; substituted or non-substituted $C_3$-$C_7$-cycloalkyl; $C_3$-$C_7$-halogenocycloalkyl having 1 to 9 halogen atoms; substituted or non-substituted ($C_3$-$C_7$-cycloalkyl)-$C_1$-$C_8$-alkyl; substituted or non-substituted $C_4$-$C_7$-cycloalkenyl; $C_4$-$C_7$-halogenocycloalkenyl having 1 to 9 halogen atoms; substituted or non-substituted ($C_3$-$C_7$-cycloalkyl)-$C_2$-$C_8$-alkenyl; substituted or non-substituted ($C_3$-$C_7$-cycloalkyl)-$C_2$-$C_8$-alkynyl; substituted or non-substituted bicyclo[2.2.1]heptanyl; substituted or non-substituted bicyclo[2.2.1]heptenyl; substituted or non-substituted tri($C_1$-$C_8$)alkylsilyl; substituted or non-substituted tri ($C_1$-$C_8$)alkylsilyl-$C_1$-$C_8$-alkyl; substituted or non-substituted $C_1$-$C_8$-alkylcarbonyl; $C_1$-$C_8$-halogenoalkylcarbonyl having 1 to 9 halogen atoms; substituted or non-substituted $C_1$-$C_8$-alkylcarbonyloxy; $C_1$-$C_8$-halogenoalkylcarbonyloxy having 1 to 9 halogen atoms; substituted or non-substituted $C_1$-$C_8$-alkylcarbonylamino $C_1$-$C_8$-halogenoalkylcarbonylamino having 1 to 9 halogen atoms; substituted or non-substituted $C_1$-$C_8$-alkoxycarbonyl; $C_1$-$C_8$-halogenoalkoxycarbonyl having 1 to 9 halogen atoms; substituted or non-substituted $C_1$-$C_8$-alkyloxycarbonyloxy $C_1$-$C_8$-halogenoalkoxycarbonyloxy having 1 to 9 halogen atoms; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl that can be substituted by up to 6 groups Q which can be the same or different; $C_1$-$C_8$-arylalkyl that can be substituted by up to 6 groups Q which can be the same or different; $C_2$-$C_8$-arylalkenyl that can be substituted by up to 6 groups Q which can be the same or different; $C_2$-$C_8$-arylalkynyl that can be substituted by up to 6 groups Q which can be the same or different; aryloxy that can be substituted by up to 6 groups Q which can be the same or different; arylsulfanyl that can be substituted by up to 6 groups Q which can be the same or different; arylamino that can be substituted by up to 6 groups Q which can be the same or different; $C_1$-$C_8$-arylalkyloxy that can be substituted by up to 6 groups Q which can be the same or different; $C_1$-$C_8$-arylalkylsulfanyl that can be substituted by up to 6 groups Q which can be the same or different; $C_1$-$C_8$-arylalkylamino that can be substituted by up to 6 groups Q which can be the same or different; $C_1$-$C_8$-heteroarylalkyl that can be substituted by up to 6 groups Q which can be the same or different; heteroaryl which can be substituted by up to 4 groups Q; or heteroaryloxy which can be substituted by up to 4 groups Q;

each Y is independently a halogen atom; $C_1$-$C_8$-alkyl; $C_1$-$C_8$-halogenoalkyl having 1 to 9 halogen atoms; substituted or non-substituted $C_1$-$C_8$-alkoxy; $C_1$-$C_8$-halogenoalkoxy having 1 to 9 halogen atoms; substituted or non-substituted $C_1$-$C_8$-alkylsulfanyl; $C_1$-$C_8$-halogenoalkylsulfanyl having 1 to 9 halogen atoms; or substituted or non-substituted $C_1$-$C_8$-alkoxycarbonyl;

each Q is independently a halogen atom, cyano, nitro, substituted or non-substituted $C_1$-$C_8$-alkyl, $C_1$-$C_8$-halogenoalkyl comprising up to 9 halogen atoms that can be the same or different, substituted or non-substituted $C_1$-$C_8$-alkoxy, $C_1$-$C_8$-halogenoalkoxy comprising up to 9 halogen atoms that can be the same or different, substituted or non-substituted C₁-C₈-alkylsulfanyl, C₁-C₈-halogenoalkylsulfanyl comprising up to 9 halogen atoms that can be the same or different, substituted or non-substituted tri(C₁-C₈)alkylsilyl, substituted or non-substituted tri(C₁-C₈)alkylsilyl-C₁-C₈-alkyl, substituted or non-substituted (C₁-C₈-alkoxyimino)-C₁-C₈-alkyl, or substituted or non-substituted (benzyloxyimino)-C₁-C₈-alkyl; and R is independently hydrogen atom; halogen atom; nitro; cyano; hydroxy; amino; sulfanyl; pentafluoro-λ⁶-sulfanyl; substituted or non-substituted (C₁-C₈-alkoxyimino)-C₁-C₈-alkyl; substituted or non-substituted (benzyloxyimino)-C₁-C₈-alkyl; substituted or non-substituted C₁-C₈-alkyl; C₁-C₈-halogenoalkyl having 1 to 9 halogen atoms; substituted or non-substituted C₂-C₈-alkenyl; C₂-C₈-halogenoalkenyl having 1 to 9 halogen atoms; substituted or non-substituted C₂-C₈-alkynyl; C₂-C₈-halogenoalkynyl having 1 to 9 halogen atoms; substituted or non-substituted C₁-C₈-alkoxy; C₁-C₈-halogenoalkoxy having 1 to 9 halogen atoms; substituted or non-substituted C₁-C₈-alkylsulfanyl; C₁-C₈-halogenoalkylsulfanyl having 1 to 9 halogen atoms; substituted or non-substituted C₁-C₈-alkylsulfinyl; C₁-C₈-halogenoalkylsulfinyl having 1 to 9 halogen atoms; substituted or non-substituted C₁-C₈-alkylsulfonyl; C₁-C₈-halogenoalkylsulfonyl having 1 to 9 halogen atoms; substituted or non-substituted C₁-C₈-alkylamino; substituted or non-substituted di-C₁-C₈-alkylamino; substituted or non-substituted C₂-C₈-alkenyloxy; substituted or non-substituted C₃-C₈-alkynyloxy; substituted or non-substituted C₃-C₇-cycloalkyl; C₃-C₇-halogenocycloalkyl having 1 to 9 halogen atoms; substituted or non-substituted tri(C₁-C₈)alkylsilyl; substituted or non-substituted C₁-C₈-alkylcarbonyl; C₁-C₈-halogenoalkylcarbonyl having 1 to 9 halogen atoms; substituted or non-substituted C₁-C₈-alkoxycarbonyl; C₁-C₈-halogenoalkoxycarbonyl having 1 to 9 halogen atoms; substituted or non-substituted C₁-C₈-alkylcarbamoyl; substituted or non-substituted di-C₁-C₈-alkylcarbamoyl; phenoxy; phenylsulfanyl; phenylamino; benzyloxy; benzylsulfanyl; or benzylamino, or a salt, an N-oxide, a metal complex, a metalloid complex, an optically active isomer, or a geometric isomer thereof.

2. The compound according to claim 1, wherein A is selected from the group consisting of:

a heterocycle of formula (A¹)

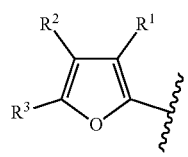

(A¹)

wherein:

R¹, R² and R³ are independently a hydrogen atom; a halogen atom; substituted or non-substituted C₁-C₅-alkyl; C₁-C₅-halogenoalkyl comprising up to 9 halogen atoms that can be the same or different; substituted or non-substituted C₁-C₅-alkoxy or C₁-C₅-halogenoalkoxy comprising up to 9 halogen atoms that can be the same or different;

a heterocycle of formula (A²)

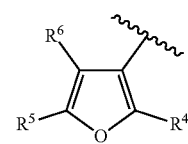

(A²)

wherein:

R⁴, R⁵ and R⁶ are independently a hydrogen atom; a halogen atom; substituted or non-substituted C₁-C₅-alkyl; C₁-C₅-halogenoalkyl comprising up to 9 halogen atoms that can be the same or different; substituted or non-substituted C₁-C₅-alkoxy or C₁-C₅-halogenoalkoxy comprising up to 9 halogen atoms that can be the same or different;

a heterocycle of formula (A³)

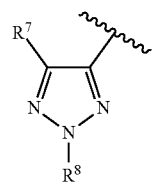

(A³)

wherein:

R⁷ is a hydrogen atom; a halogen atom; substituted or non-substituted C₁-C₅-alkyl; C₁-C₅-halogenoalkyl comprising up to 9 halogen atoms that can be the same or different; substituted or non-substituted C₁-C₅-alkoxy or C₁-C₅-halogenoalkoxy comprising up to 9 halogen atoms that can be the same or different;

R⁸ is a hydrogen atom or a substituted or non-substituted C₁-C₅-alkyl;

a heterocycle of formula (A⁴)

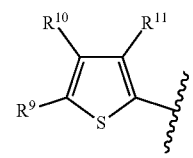

(A⁴)

wherein:

R⁹, R¹⁰ and R¹¹ are independently a hydrogen atom; a halogen atom; substituted or non-substituted C₁-C₅-alkyl; amino; substituted or non-substituted C₁-C₅-alkoxy; substituted or non-substituted C₁-C₅-alkylsulfanyl; C₁-C₅-halogenoalkyl comprising up to 9 halogen atoms that can be the same or different or C₁-C₅-halogenoalkoxy comprising up to 9 halogen atoms that can be the same or different;

a heterocycle of formula (A⁵)

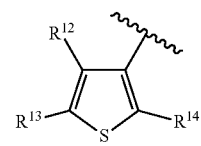

(A⁵)

wherein:

$R^{12}$ and $R^{13}$ are independently a hydrogen atom; a halogen atom; substituted or non-substituted $C_1$-$C_5$-alkyl; substituted or non-substituted $C_1$-$C_5$-alkoxy; amino; $C_1$-$C_5$-halogenoalkyl comprising up to 9 halogen atoms that can be the same or different or $C_1$-$C_5$-halogenoalkoxy comprising up to 9 halogen atoms that can be the same or different;

$R^{14}$ is a hydrogen atom; a halogen atom; substituted or non-substituted $C_1$-$C_5$-alkyl; substituted or non-substituted $C_1$-$C_5$-alkoxy; amino; $C_1$-$C_5$-halogenoalkyl comprising up to 9 halogen atoms that can be the same or different or $C_1$-$C_5$-halogenoalkoxy comprising up to 9 halogen atoms that can be the same or different;

a heterocycle of formula ($A^6$)

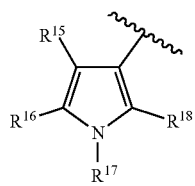

wherein:

$R^{15}$ is a hydrogen atom; a halogen atom; a cyano; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

$R^{16}$ and $R^{18}$ are independently a hydrogen atom; a halogen atom; substituted or non-substituted $C_1$-$C_5$-alkoxycarbonyl; substituted or non-substituted $C_1$-$C_5$-alkyl; $C_1$-$C_5$-halogenoalkoxy comprising up to 9 halogen atoms that can be the same or different or $C_1$-$C_5$-halogenoalkyl comprising up to 9 halogen atoms that can be the same or different;

$R^{17}$ represent is a hydrogen atom or substituted or non-substituted $C_1$-$C_5$-alkyl;

a heterocycle of formula ($A^7$)

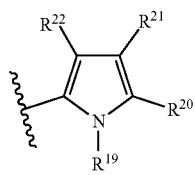

wherein:

$R^{19}$ is a hydrogen atom or a $C_1$-$C_5$-alkyl $R^{20}$, $R^{21}$ and $R^{22}$ are independently a hydrogen atom; a halogen atom; substituted or non-substituted $C_1$-$C_5$-alkyl or $C_1$-$C_5$-halogenoalkyl comprising up to 9 halogen atoms that can be the same or different;

a heterocycle of formula ($A^8$)

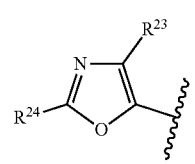

wherein:

$R^{23}$ is a hydrogen atom; a halogen atom; substituted or non-substituted $C_1$-$C_5$-alkyl or $C_1$-$C_5$-halogenoalkyl comprising up to 9 halogen atoms that can be the same or different;

$R^{24}$ is a hydrogen atom or substituted or non-substituted $C_1$-$C_5$-alkyl or $C_1$-$C_5$-halogenoalkyl comprising up to 9 halogen atoms that can be the same or different;

a heterocycle of formula ($A^9$)

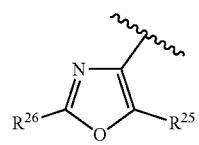

wherein:

$R^{25}$ is a hydrogen atom; a halogen atom; substituted or non-substituted $C_1$-$C_5$-alkyl or $C_1$-$C_5$-halogenoalkyl comprising up to 9 halogen atoms that can be the same or different;

$R^{26}$ is a hydrogen atom; substituted or non-substituted $C_1$-$C_5$-alkyl or $C_1$-$C_5$-halogenoalkyl comprising up to 9 halogen atoms that can be the same or different;

a heterocycle of formula ($A^m$)

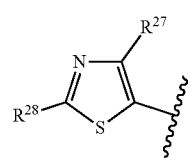

wherein:

$R^{27}$ is a hydrogen atom; a halogen atom; substituted or non-substituted $C_1$-$C_5$-alkyl or $C_1$-$C_5$-halogenoalkyl comprising up to 9 halogen atoms that can be the same or different;

$R^{28}$ is a hydrogen atom; a halogen atom; substituted or non-substituted $C_1$-$C_5$-alkyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or substituted or non-substituted di($C_1$-$C_5$-alkyl)amino;

a heterocycle of formula ($A^{11}$)

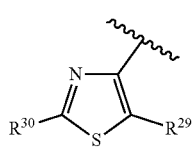

wherein:

$R^{29}$ is a hydrogen atom; a halogen atom; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

$R^{30}$ is a hydrogen atom; a halogen atom; substituted or non-substituted $C_1$-$C_5$-alkyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or substituted or non-substituted di($C_1$-$C_5$-alkyl)amino;

a heterocycle of formula ($A^{12}$)

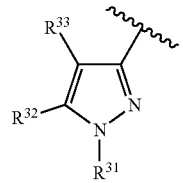

($A^{12}$)

wherein:
$R^{31}$ is a hydrogen atom or a substituted or non-substituted $C_1$-$C_5$-alkyl
$R^{32}$ is a hydrogen atom; a halogen atom; substituted or non-substituted $C_1$-$C_5$-alkyl or $C_1$-$C_5$-halogenoalkyl comprising up to 9 halogen atoms that can be the same or different;
$R^{33}$ is a hydrogen atom; a halogen atom; a nitro; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;

a heterocycle of formula ($A^{13}$)

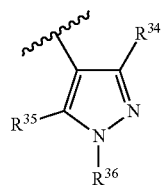

($A^{13}$)

wherein:
$R^{34}$ is a hydrogen atom; a halogen atom; substituted or non-substituted $C_1$-$C_5$-alkyl; substituted or non-substituted $C_3$-$C_5$-cycloalkyl; $C_1$-$C_5$-halogenoalkyl comprising up to 9 halogen atoms that can be the same or different; substituted or non-substituted $C_1$-$C_5$-alkoxy; substituted or non-substituted $C_2$-$C_5$-alkynyloxy or $C_1$-$C_5$-halogenoalkoxy comprising up to 9 halogen atoms that can be the same or different;
$R^{35}$ is a hydrogen atom; a halogen atom; substituted or non-substituted $C_1$-$C_5$-alkyl; a cyano; substituted or non-substituted $C_1$-$C_5$-alkoxy; substituted or non-substituted $C_1$-$C_5$-alkylsulfanyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or substituted or non-substituted di($C_1$-$C_5$-alkyl)amino;
$R^{36}$ is a hydrogen atom or substituted or non-substituted $C_1$-$C_5$-alkyl;
provided that $R^{35}$ is not a fluoro or a chloro atom when $R^{34}$ simultaneously is a difluoromethyl or a dichloromethyl group and $R^{36}$ simultaneously is a methyl group;

a heterocycle of formula ($A^{14}$)

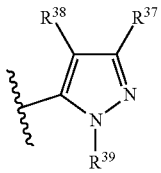

($A^{14}$)

wherein:
$R^{37}$ and $R^{38}$ are independently a hydrogen atom; a halogen atom; substituted or non-substituted $C_1$-$C_5$-alkyl; $C_1$-$C_5$-halogenoalkyl comprising up to 9 halogen atoms that can be the same or different; substituted or non-substituted $C_1$-$C_5$-alkoxy or a substituted or non-substituted $C_1$-$C_5$-alkylsulfanyl;
$R^{39}$ is a hydrogen atom or substituted or non-substituted $C_1$-$C_5$-alkyl;

a heterocycle of formula ($A^{15}$)

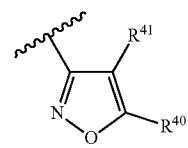

($A^{15}$)

wherein:
$R^{40}$ and $R^{41}$ are independently a hydrogen atom; a halogen atom; substituted or non-substituted $C_1$-$C_5$-alkyl or $C_1$-$C_5$-halogenoalkyl comprising up to 9 halogen atoms that can be the same or different;

a heterocycle of formula ($A^{16}$)

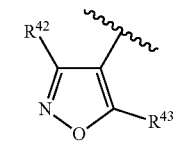

($A^{16}$)

wherein:
$R^{42}$ and $R^{43}$ are independently a hydrogen atom; a halogen atom; substituted or non-substituted $C_1$-$C_5$-alkyl; $C_1$-$C_5$-halogenoalkyl comprising up to 9 halogen atoms that can be the same or different or amino;

a heterocycle of formula ($A^{17}$)

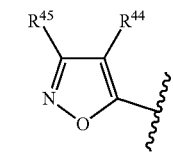

($A^{17}$)

wherein:
$R^{44}$ and $R^{45}$ are independently a hydrogen atom; a halogen atom; substituted or non-substituted $C_1$-$C_5$-alkyl or $C_1$-$C_5$-halogenoalkyl comprising up to 9 halogen atoms that can be the same or different;

a heterocycle of formula ($A^{18}$)

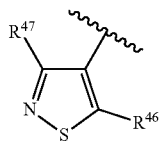
($A^{18}$)

wherein:
$R^{47}$ is a hydrogen atom; a halogen atom; substituted or non-substituted $C_1$-$C_5$-alkyl or $C_1$-$C_5$-halogenoalkyl comprising up to 9 halogen atoms that can be the same or different;
$R^{46}$ is a hydrogen atom; a halogen atom; substituted or non-substituted $C_1$-$C_5$-alkyl; $C_1$-$C_5$-halogenoalkyl comprising up to 9 halogen atoms that can be the same or different or substituted or non-substituted $C_1$-$C_5$-alkylsulfanyl;
  a heterocycle of formula ($A^{19}$)

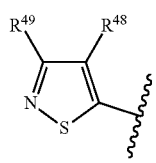
($A^{19}$)

wherein:
$R^{49}$ and $R^{48}$ are independently a hydrogen atom; a halogen atom; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;
  a heterocycle of formula ($A^{20}$)

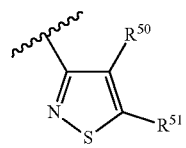
($A^{20}$)

wherein:
$R^{50}$ and $R^{51}$ are independently a hydrogen atom; a halogen atom; substituted or non-substituted $C_1$-$C_5$-alkyl; substituted or non-substituted $C_1$-$C_5$-alkoxy; $C_1$-$C_5$-halogenoalkoxy comprising up to 9 halogen atoms that can be the same or different or $C_1$-$C_5$-halogenoalkyl comprising up to 9 halogen atoms that can be the same or different;
  a heterocycle of formula ($A^{21}$)

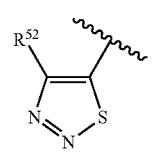
($A^{21}$)

wherein:
$R^{52}$ is a hydrogen atom; a halogen atom; substituted or non-substituted $C_1$-$C_5$-alkyl or $C_1$-$C_5$-halogenoalkyl comprising up to 9 halogen atoms that can be the same or different;
  a heterocycle of formula ($A^{22}$)

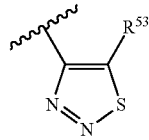
($A^{22}$)

wherein:
$R^{53}$ is a hydrogen atom; a halogen atom; substituted or non-substituted $C_1$-$C_5$-alkyl or $C_1$-$C_5$-halogenoalkyl comprising up to 9 halogen atoms that can be the same or different;
  a heterocycle of formula ($A^{23}$)

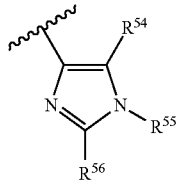
($A^{23}$)

wherein:
$R^{54}$ and $R^{56}$ are independently a hydrogen atom; a halogen atom; substituted or non-substituted $C_1$-$C_5$-alkyl or $C_1$-$C_5$-halogenoalkyl comprising up to 9 halogen atoms that can be the same or different;
$R^{55}$ is a hydrogen atom or substituted or non-substituted $C_1$-$C_5$-alkyl;
  a heterocycle of formula ($A^{24}$)

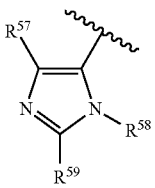
($A^{24}$)

wherein:
$R^{57}$ and $R^{59}$ are independently a hydrogen atom; a halogen atom; substituted or non-substituted $C_1$-$C_5$-alkyl or $C_1$-$C_5$-halogenoalkyl comprising up to 9 halogen atoms that can be the same or different;
$R^{58}$ is a hydrogen atom or substituted or non-substituted $C_1$-$C_5$-alkyl;

a heterocycle of formula (A²⁵)

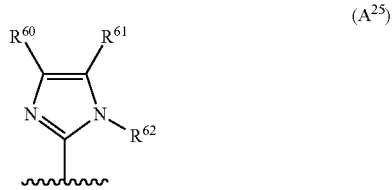

wherein:
$R^{60}$ and $R^{61}$ are independently a hydrogen atom; a halogen atom; substituted or non-substituted $C_1$-$C_5$-alkyl or $C_1$-$C_5$-halogenoalkyl comprising up to 9 halogen atoms that can be the same or different;
$R^{62}$ is a hydrogen atom or substituted or non-substituted $C_1$-$C_5$-alkyl; and
a heterocycle of formula (A²⁶)

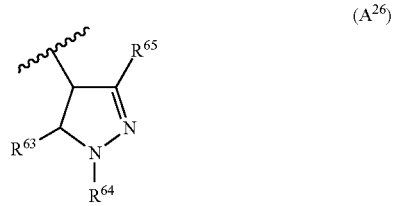

wherein:
$R^{65}$ is a hydrogen atom; a halogen atom; substituted or non-substituted $C_1$-$C_5$-alkyl; substituted or non-substituted $C_3$-$C_5$-cycloalkyl; $C_1$-$C_5$-halogenoalkyl comprising up to 9 halogen atoms that can be the same or different; substituted or non-substituted $C_1$-$C_5$-alkoxy; substituted or non-substituted $C_2$-$C_5$-alkynyloxy or $C_1$-$C_5$-halogenoalkoxy comprising up to 9 halogen atoms that can be the same or different;
$R^{63}$ is a hydrogen atom; a halogen atom; substituted or non-substituted $C_1$-$C_5$-alkyl; a cyano; substituted or non-substituted $C_1$-$C_5$-alkoxy; substituted or non-substituted $C_1$-$C_5$-alkylsulfanyl; $C_1$-$C_5$-halogenoalkyl comprising up to 9 halogen atoms that can be the same or different; $C_1$-$C_5$-halogenoalkoxy comprising up to 9 halogen atoms that can be the same or different; amino; substituted or non-substituted $C_1$-$C_5$-alkylamino or di($C_1$-$C_5$-alkyl)amino;
$R^{64}$ is a hydrogen atom or substituted or non-substituted $C_1$-$C_5$-alkyl,
or a salt, an N-oxide, a metal complex, a metalloid complex, an optically active isomer, or a geometric isomer thereof.

3. The compound according to claim 2, or a salt, an N-oxide, a metal complex, a metalloid complex, an optically active isomer, or a geometric isomer thereof, wherein A is selected from the group consisting of A²; A⁵; A⁶; A¹⁰ and A¹³.

4. The compound according to claim 2, or a salt, an N-oxide, a metal complex, a metalloid complex, an optically active isomer, or a geometric isomer thereof, wherein A is A¹³ and wherein:
$R^{34}$ is a substituted or non-substituted $C_1$-$C_5$-alkyl, $C_1$-$C_5$-halogenoalkyl comprising up to 9 halogen atoms that can be the same or different; substituted or non-substituted $C_1$-$C_5$-alkoxy;
$R^{35}$ is a hydrogen atom or a halogen atom; and
$R^{36}$ is a substituted or non-substituted $C_1$-$C_5$-alkyl.

5. The compound according to claim 1, or a salt, an N-oxide, a metal complex, a metalloid complex, an optically active isomer, or a geometric isomer thereof, wherein $Z^1$ is a non-substituted cyclopropyl or a cyclopropyl substituted by 1 or 2 $C_1$-$C_5$-alkyl.

6. The compound according to claim 1, or a salt, an N-oxide, a metal complex, a metalloid complex, an optically active isomer, or a geometric isomer thereof, wherein $Z^2$ and $Z^3$ are independently a hydrogen atom or a methyl.

7. The compound according to claim 1, or a salt, an N-oxide, a metal complex, a metalloid complex, an optically active isomer, or a geometric isomer thereof, wherein n is 0, 1 or 2.

8. The compound according to claim 1, or a salt, an N-oxide, a metal complex, a metalloid complex, an optically active isomer, or a geometric isomer thereof, wherein m is 0, 1, 2, 3 or 4.

9. The compound according to claim 1, or a salt, an N-oxide, a metal complex, a metalloid complex, an optically active isomer, or a geometric isomer thereof, wherein p is 1, 3 or 4.

10. The compound according to claim 1, or a salt, an N-oxide, a metal complex, a metalloid complex, an optically active isomer, or a geometric isomer thereof, wherein $Z^4$ is a halogen, non-substituted $C_1$-$C_4$-alkyl, $C_1$-$C_4$-halogenoalkyl having 1 to 3 halogen atoms, non-substituted $C_1$-$C_4$-alkyloxy, $C_1$-$C_4$-halogenoalkyloxy having 1 to 3 halogen atoms, substituted or non-substituted cyclopropyl, substituted or non-substituted $C_2$-$C_4$-alkenyl or substituted or non-substituted $C_2$-$C_4$-alkynyl.

11. The compound according to claim 1, or a salt, an N-oxide, a metal complex, a metalloid complex, an optically active isomer, or a geometric isomer thereof, wherein $B^1$ is a thienyl ring; a benzothiophenyl ring; a pyridinyl ring; a furanyl ring; or a benzofuranyl ring.

12. The compound according to claim 1, or a salt, an N-oxide, a metal complex, a metalloid complex, an optically active isomer, or a geometric isomer thereof, wherein each W is independently a halogen atom; non-substituted $C_1$-$C_8$-alkyl; $C_1$-$C_8$-halogenoalkyl comprising up to 9 halogen atoms which can be the same or different; substituted or non-substituted $C_2$-$C_8$-alkenyl; substituted or non-substituted $C_5$-$C_7$-cycloalkenyl; substituted or non-substituted $C_3$-$C_7$-cycloalkyl; tri($C_1$-$C_8$-alkyl)silyl; substituted or non-substituted $C_1$-$C_8$-alkoxy; or substituted or non-substituted $C_1$-$C_8$-alkylsulfanyl.

13. The compound according to claim 1, or a salt, an N-oxide, a metal complex, a metalloid complex, an optically active isomer, or a geometric isomer thereof, wherein each Y is independently a halogen or a substituted or non-substituted $C_1$-$C_8$-alkyl.

14. A fungicide composition comprising, as an active ingredient, an effective amount of a compound of formula (I) according to claim 1, or a salt, an N-oxide, a metal complex, a metalloid complex, an optically active isomer, or a geometric isomer thereof and an agriculturally acceptable support, carrier or filler.

15. A method for controlling phytopathogenic fungi of crops, comprising applying an agronomically effective and substantially non-phytotoxic quantity of a compound according to claim 1, or a salt, an N-oxide, a metal complex, a metalloid complex, an optically active isomer, or a geometric isomer thereof, to the soil where plants grow or are capable of growing, to the leaves and/or the fruit of plants or to the seeds of plants.

16. A method for controlling phytopathogenic fungi of crops, comprising applying an agronomically effective and substantially non-phytotoxic quantity of a composition according to claim 14 to the soil where plants grow or are capable of growing, to the leaves and/or the fruit of plants or to the seeds of plants.

17. A process for producing compositions for controlling phytopathogenic harmful fungi, wherein the compound of formula (I) according to claim 1, or a salt, an N-oxide, a metal complex, a metalloid complex, an optically active isomer, or a geometric isomer thereof, is mixed with extenders and/or surfactants.

* * * * *